(12) United States Patent
Dhillon et al.

(10) Patent No.: US 10,136,998 B2
(45) Date of Patent: Nov. 27, 2018

(54) REVISION TOTAL ANKLE IMPLANTS

(71) Applicant: Wright Medical Technology, Inc., Memphis, TN (US)

(72) Inventors: Braham K. Dhillon, Memphis, TN (US); Elizabeth J. Sander, Memphis, TN (US); Daniel E. Free, Arlington, TN (US); Robert M. Howles, Bartlett, TN (US); Ramon Luna, Arlington, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 15/251,830

(22) Filed: Aug. 30, 2016

(65) Prior Publication Data

US 2018/0055648 A1    Mar. 1, 2018

(51) Int. Cl.
*A61F 2/42* (2006.01)
*A61F 2/30* (2006.01)

(52) U.S. Cl.
CPC ........ *A61F 2/4202* (2013.01); *A61F 2/30734* (2013.01); *A61F 2002/3069* (2013.01); *A61F 2002/30224* (2013.01); *A61F 2002/30247* (2013.01); *A61F 2002/30299* (2013.01); *A61F 2002/30405* (2013.01); *A61F 2002/30433* (2013.01); *A61F 2002/30604* (2013.01); *A61F 2002/30607* (2013.01); *A61F 2002/30616* (2013.01); *A61F 2002/30736* (2013.01); *A61F 2002/4205* (2013.01); *A61F 2002/4207* (2013.01); *A61F 2002/4217* (2013.01)

(58) Field of Classification Search
CPC ............... A61F 2/30734; A61F 2/4202; A61F 2002/30736; A61F 2002/4207; A61F 2002/30433; A61F 2002/30604; A61F 2002/30616; A61F 2002/3069
See application file for complete search history.

(56) References Cited

U.S. PATENT DOCUMENTS

| | | |
|---|---|---|
| 1,090,881 A | 3/1914 | Rowley |
| 3,872,519 A | 3/1975 | Giannestras et al. |
| 3,889,300 A | 6/1975 | Smith |
| 3,896,502 A | 7/1975 | Lennox |

(Continued)

FOREIGN PATENT DOCUMENTS

| | | |
|---|---|---|
| FR | 2220235 A1 | 4/1974 |
| JP | H08-501716 A | 2/1996 |

(Continued)

OTHER PUBLICATIONS

Official Action in Japanese Patent Appln. No. 2008-501935, dated Dec. 22, 2010.

(Continued)

*Primary Examiner* — Marcia Watkins
(74) *Attorney, Agent, or Firm* — Duane Morris LLP

(57) ABSTRACT

In some embodiments, a revision implant includes a body extending between a first planar surface and a second planar surface and a head extending from the first planar surface of the body. The head is configured to couple the revision implant to at least one additional component of a multi-component prosthesis. At least one coupling mechanism is configured to couple the body to a first bone.

6 Claims, 30 Drawing Sheets

(56) References Cited

U.S. PATENT DOCUMENTS

| | | |
|---|---|---|
| 3,896,503 A | 7/1975 | Freeman et al. |
| 3,975,778 A | 8/1976 | Newton, III |
| 3,987,500 A | 10/1976 | Schlein |
| 4,156,944 A | 6/1979 | Schreiber et al. |
| 4,166,292 A | 9/1979 | Bokros et al. |
| 4,229,839 A | 10/1980 | Schwemmer |
| 4,232,404 A | 11/1980 | Samuelson et al. |
| 4,470,158 A * | 9/1984 | Pappas ................ A61F 2/3804 623/20.2 |
| 4,553,273 A | 11/1985 | Wu |
| 4,676,797 A | 6/1987 | Anapliotis et al. |
| 4,713,003 A | 12/1987 | Symington |
| 4,822,364 A | 4/1989 | Inglis |
| 4,827,496 A | 5/1989 | Cheney |
| 4,944,757 A * | 7/1990 | Martinez ................ A61F 2/389 623/20.15 |
| 5,041,139 A | 8/1991 | Branemark |
| 5,326,365 A | 7/1994 | Alvine |
| 5,397,360 A | 3/1995 | Cohen et al. |
| 5,713,901 A | 2/1998 | Tock |
| 5,766,259 A | 6/1998 | Sammarco |
| 5,782,920 A | 7/1998 | Colleran |
| 5,824,106 A | 10/1998 | Fournol |
| 6,102,956 A | 8/2000 | Kranz |
| 6,110,172 A | 8/2000 | Jackson |
| 6,136,032 A | 10/2000 | Viladot Pence et al. |
| 6,139,584 A | 10/2000 | Ochoa et al. |
| 6,168,631 B1 | 1/2001 | Maxwell et al. |
| 6,488,712 B1 | 12/2002 | Tournier et al. |
| 6,589,281 B2 | 7/2003 | Hyde, Jr. |
| 6,663,669 B1 | 12/2003 | Reiley |
| 6,699,290 B1 | 3/2004 | Wack |
| 6,875,236 B2 | 4/2005 | Reiley |
| 6,926,739 B1 | 8/2005 | O'Connor et al. |
| 7,534,246 B2 | 5/2009 | Reiley et al. |
| 8,128,627 B2 | 3/2012 | Justin |
| 8,715,362 B2 | 5/2014 | Reiley et al. |
| 9,144,506 B2 | 9/2015 | Phelps |
| 9,622,871 B2 * | 4/2017 | Sander ................ A61F 2/42 |
| 2002/0055744 A1 | 5/2002 | Reiley |
| 2002/0095214 A1 | 7/2002 | Hyde, Jr. |
| 2002/0115742 A1 | 8/2002 | Trieu et al. |
| 2003/0149485 A1 | 8/2003 | Tornier |
| 2003/0204263 A1 | 10/2003 | Justin et al. |
| 2003/0204266 A1 | 10/2003 | Gerbec |
| 2004/0102854 A1 | 5/2004 | Zhu |
| 2004/0122440 A1 | 6/2004 | Daniels et al. |
| 2004/0122523 A1 | 6/2004 | Guzman |
| 2004/0143336 A1 | 7/2004 | Burkinshaw |
| 2004/0172138 A1 | 9/2004 | May et al. |
| 2004/0193278 A1 | 9/2004 | Maroney et al. |
| 2005/0049711 A1 | 3/2005 | Ball |
| 2005/0071014 A1 | 3/2005 | Barnett |
| 2005/0107882 A1 | 5/2005 | Stone |
| 2005/0192673 A1 | 9/2005 | Saltzman et al. |
| 2005/0288792 A1 | 12/2005 | Landes et al. |
| 2006/0100714 A1 | 5/2006 | Ensign |
| 2006/0200141 A1 | 9/2006 | Janna |
| 2006/0229615 A1 | 10/2006 | Abdou |
| 2006/0229730 A1 | 10/2006 | Reiley |
| 2007/0288097 A1 | 12/2007 | Hurowitz |
| 2008/0103603 A1 | 5/2008 | Hintermann |
| 2008/0119934 A1 | 5/2008 | Eckhardt |
| 2008/0140130 A1 | 6/2008 | Chan |
| 2008/0167722 A1 | 7/2008 | Metzger et al. |
| 2009/0137946 A1 | 5/2009 | Nassiri et al. |
| 2009/0182433 A1 | 7/2009 | Reiley et al. |
| 2009/0192621 A1 | 7/2009 | Winslow et al. |
| 2011/0035019 A1 | 2/2011 | Goswami et al. |
| 2011/0153024 A1 | 6/2011 | Wagner |
| 2011/0184527 A1 | 7/2011 | Vanasse |
| 2011/0190899 A1 * | 8/2011 | Pierce ................ A61F 2/30 623/20.32 |
| 2011/0295380 A1 | 12/2011 | Long |
| 2012/0010719 A1 | 1/2012 | Reiley |
| 2012/0078376 A1 * | 3/2012 | Vanasse ................ A61F 2/4261 623/21.12 |
| 2012/0245701 A1 | 9/2012 | Zak et al. |
| 2012/0259338 A1 | 10/2012 | Carr et al. |
| 2013/0053974 A1 | 2/2013 | Schultz et al. |
| 2014/0277538 A1 | 9/2014 | Sander |
| 2014/0296995 A1 | 10/2014 | Reiley et al. |
| 2015/0100132 A1 | 4/2015 | Vanasse et al. |
| 2015/0250602 A1 * | 9/2015 | Sikora ................ A61F 2/40 623/19.12 |
| 2016/0051369 A1 | 2/2016 | Sander |

FOREIGN PATENT DOCUMENTS

| | | |
|---|---|---|
| JP | H11-513274 A | 3/1997 |
| JP | 2004-202232 A | 7/2004 |
| JP | 2004-521685 A | 7/2004 |
| JP | 2004-298638 A | 10/2004 |
| JP | 2008-539922 A | 11/2008 |
| RU | 2062072 C1 | 6/1996 |
| RU | 2145822 C1 | 2/2000 |
| RU | 2149604 C1 | 5/2000 |
| RU | 2155561 C2 | 9/2000 |
| SU | 546349 A1 | 4/1977 |
| SU | 1271509 A1 | 11/1986 |
| SU | 1533685 A1 | 1/1990 |
| WO | 91/07931 A1 | 6/1991 |
| WO | 94/07440 A1 | 4/1994 |
| WO | 97/09939 A1 | 3/1997 |
| WO | 98/07380 A1 | 2/1998 |
| WO | 00/15154 A1 | 3/2000 |
| WO | 01/19294 A1 | 3/2001 |
| WO | 02/067811 A2 | 9/2002 |
| WO | 2007/082810 A2 | 7/2007 |
| WO | 2011/146617 A2 | 11/2011 |
| WO | WO2014/160703 A2 | 10/2014 |
| WO | 2014179589 A1 | 11/2014 |

OTHER PUBLICATIONS

Official Action in Australian Patent Appln. No. 2006223238, dated Oct. 15, 21010.
Supplementary European Search Report; EP Appln. No. 06737977, dated May 22, 2013.
InBone II Total Ankle System. Verified by the Wayback Machine, Dec. 24, 2011. http://www.wmt.com/footandankle/FA701-1210.asp.
European Search Report and Search Opinion issued in connection with corresponding European patent application No. EP17186960.5, dated Oct. 12, 2017, 10 pages.
Examination Report No. 1 issued in connection with corresponding Australian patent application No. 2017208278, dated Oct. 27, 2017, 9 pages.
Office Action issued in connection with corresponding Canadian Patent Application No. 2,974,569, dated May 31, 2018, 3 pages.
Official Action in corresponding Japanese Patent Application No. 2017-164316, dated Jul. 17, 2018, 4 pages.

* cited by examiner

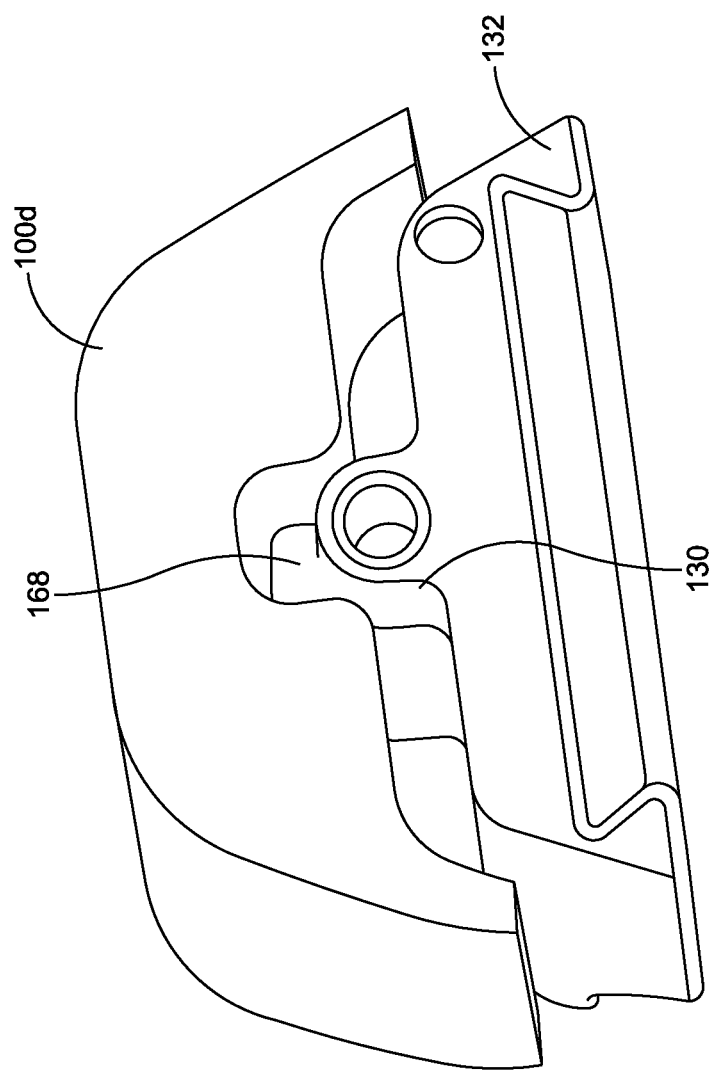

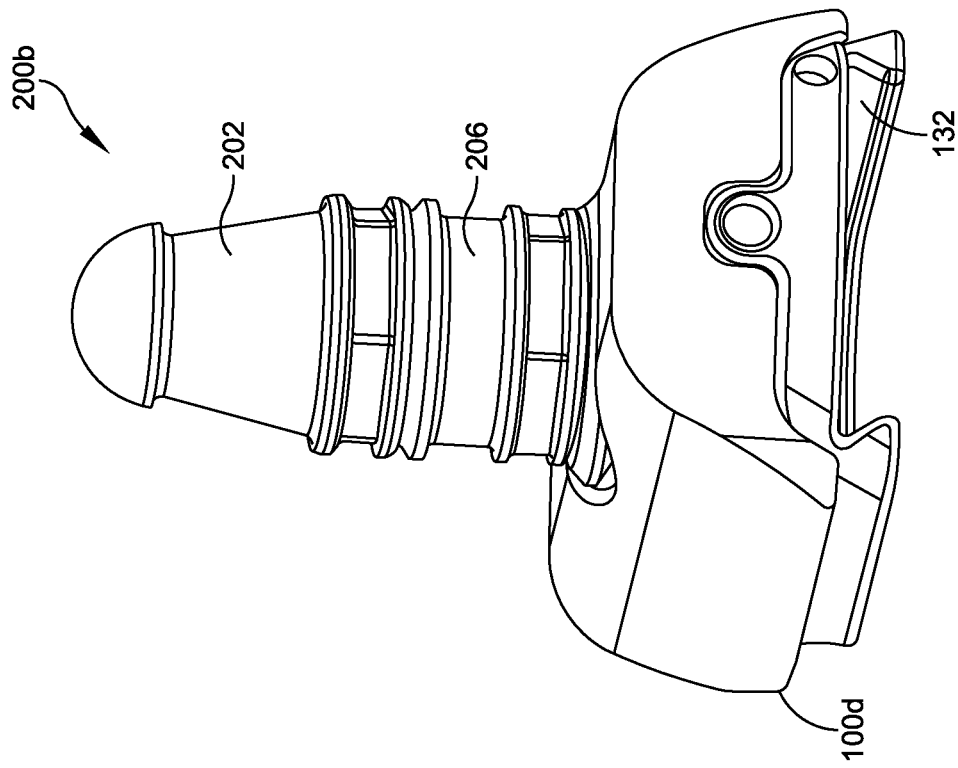
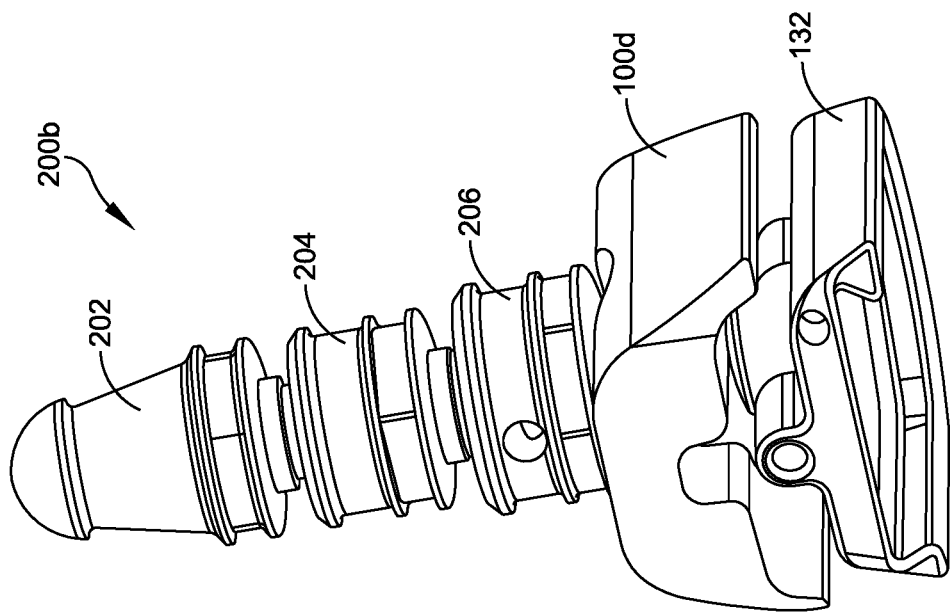
FIG. 6B
FIG. 6A

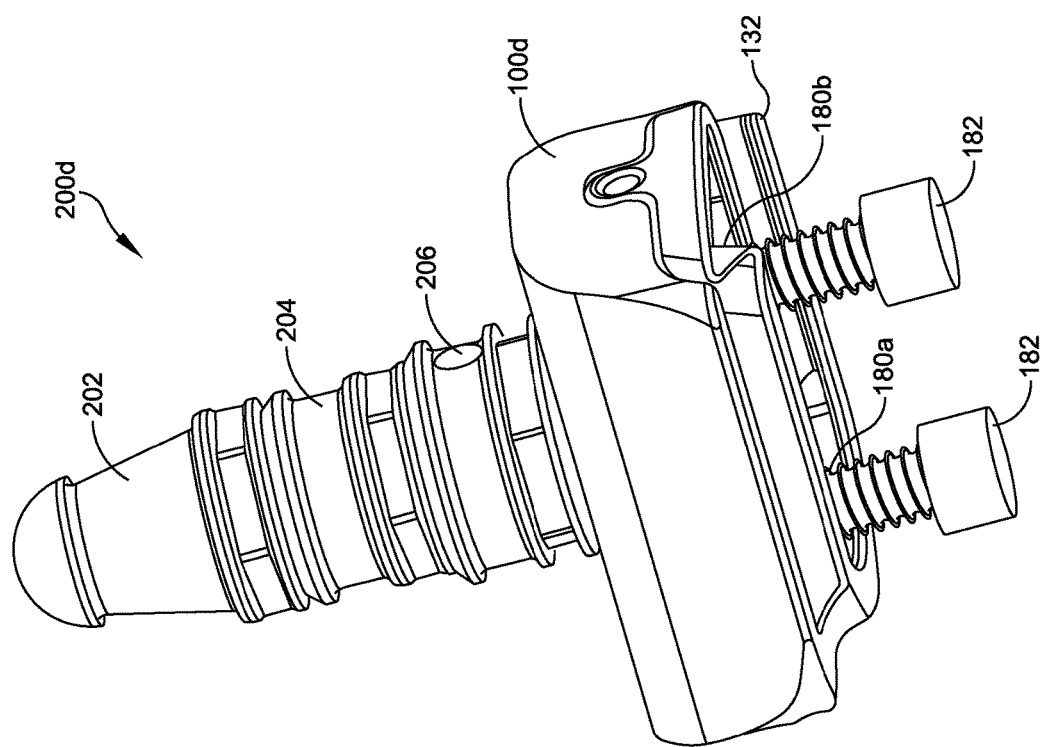

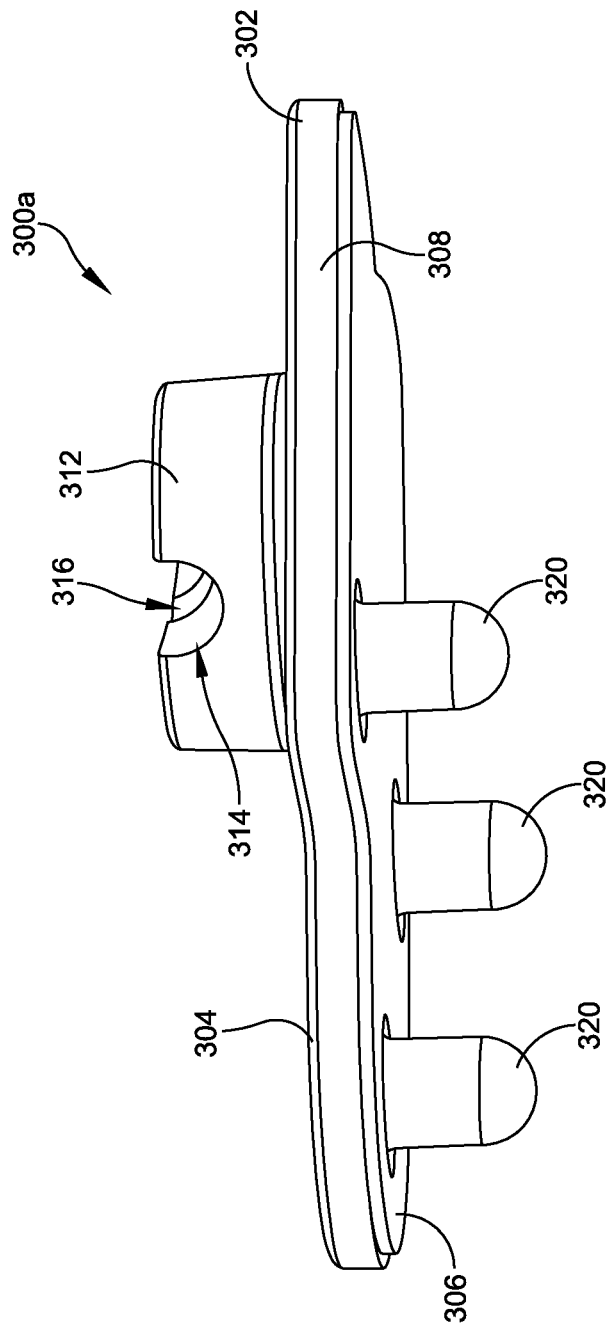

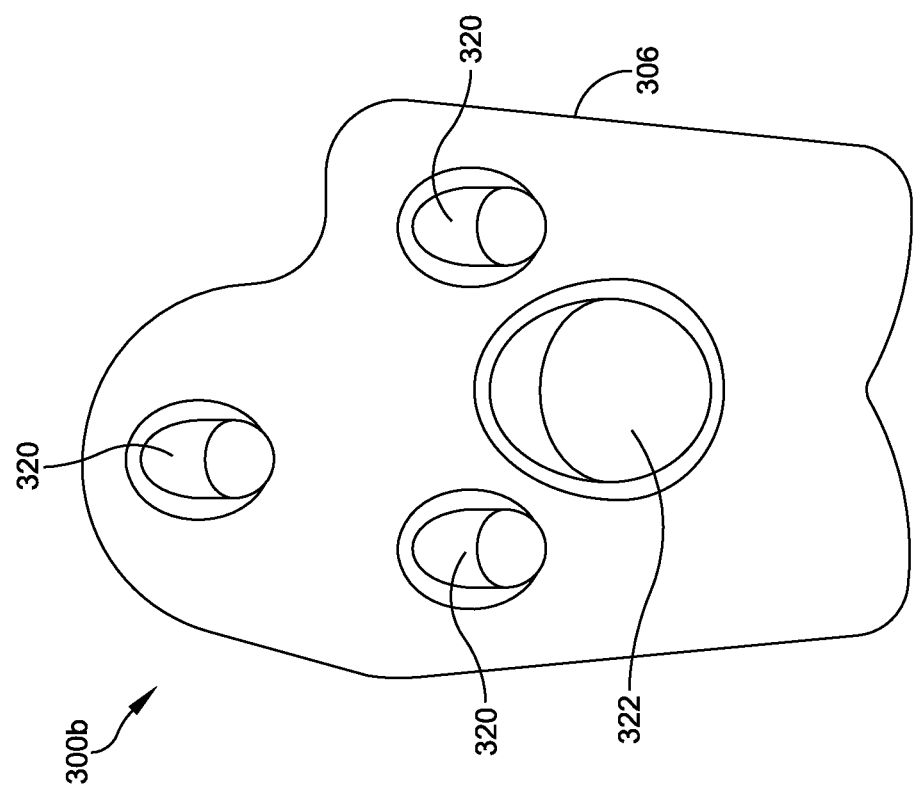

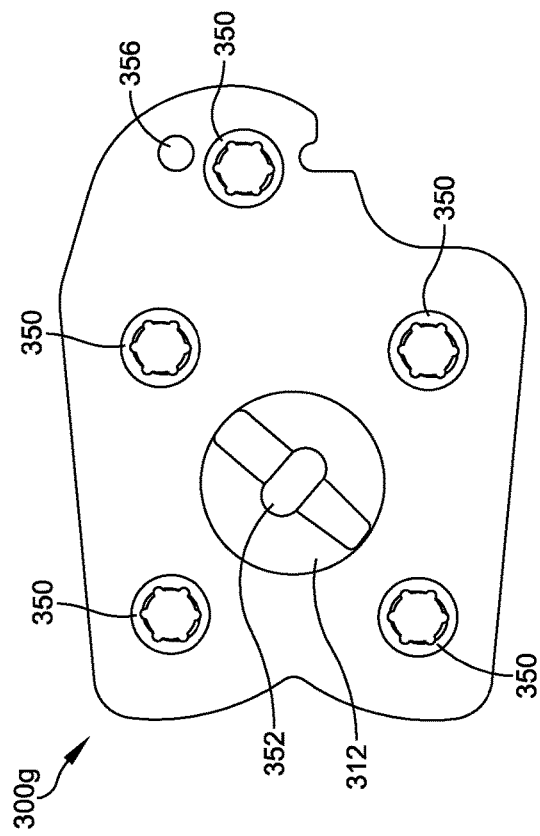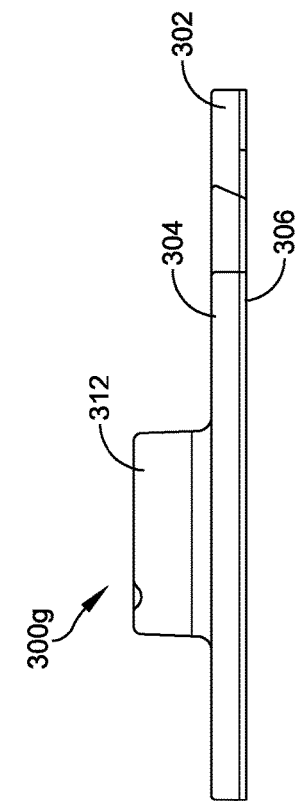

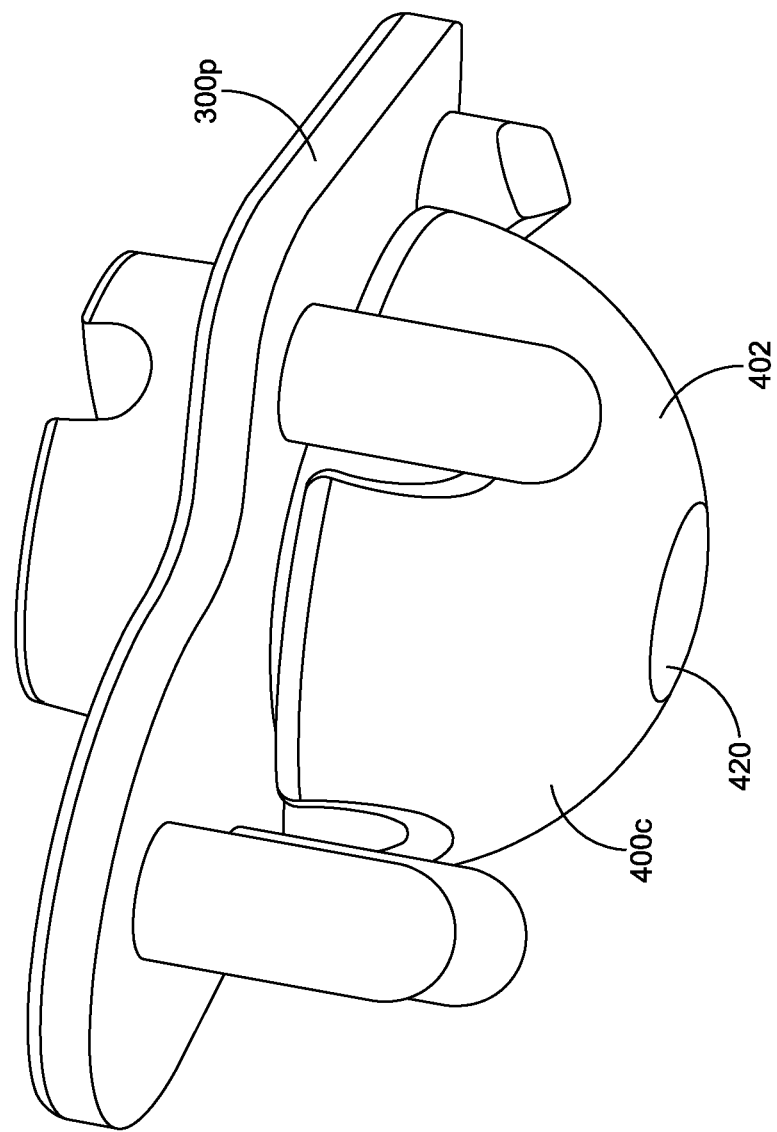

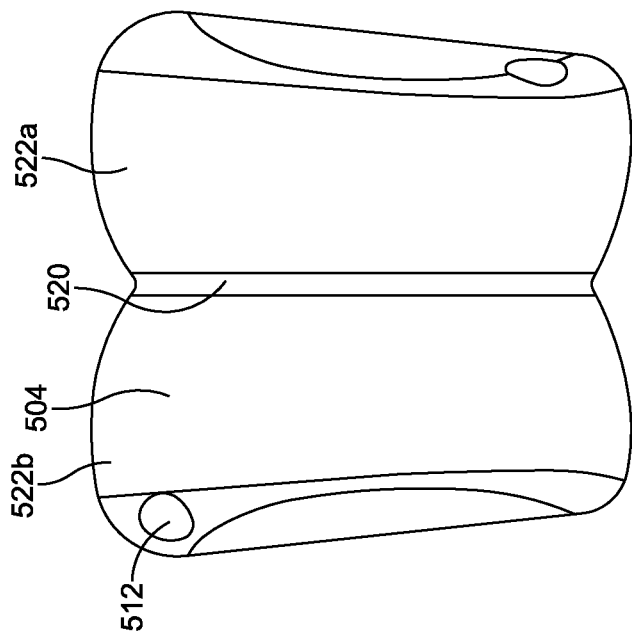
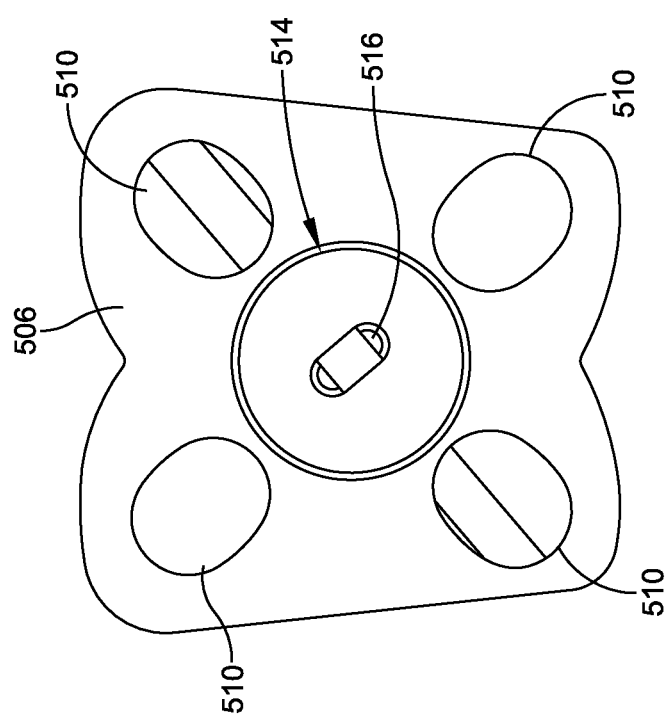
FIG. 21D
FIG. 21C

REVISION TOTAL ANKLE IMPLANTS

BACKGROUND

Total ankle replacement systems degrade over time and require replacement. In revision ankle surgery, a total ankle implant is removed and replaced with a new total ankle implant. When the primary implants are removed, a large bone void is left. The bone void is larger than the size of the primary implants removed during the total ankle replacement.

The size of a bone void cannot be determined prior to surgery using current techniques. Current ankle revision systems further require additional cuts and/or modifications of one or more ankle bones during a revision surgery. Primary components must be removed and replaced with augments, which do not provide the same fixed engagement as primary components.

SUMMARY

In various embodiments, a revision implant includes a body extending between a first planar surface and a second planar surface and a head extending from the first planar surface of the body. The head is configured to couple the revision implant to at least one additional component of a multi-component prosthesis. At least one coupling mechanism is configured to couple the body to a first bone.

In various embodiments, a surgical method is disclosed. The surgical method includes creating an incision in a patient and exposing a multi-component prosthesis implanted in a patient. At least one component of the multi-component prosthesis is disassembled and a revision implant component is coupled to a first component of the multi-component prosthesis. The revision implant component comprises a body extending between a first planar surface and a second planar surface, a head extending from the first planar surface of the body and configured to couple the revision implant to at least one additional component of a multi-component prosthesis, and at least one coupling mechanism configured to couple the body to a bone.

In various embodiments, a revision implant kit is disclosed. The revision implant kit includes a first revision implant, a second revision implant, and a third revision implant. The first revision implant includes a body extending between a first planar surface and a second planar surface, a head extending from the first planar surface of the body and configured to couple the revision implant to at least one additional component of a multi-component prosthesis, and at least one coupling mechanism configured to couple the body to a first bone. The second revision implant includes an augment configured to fill a void formed in the first bone. The second revision implant is configured to couple to the second planar surface of the body of the first revision implant. The third revision implant includes a body defining an articulation surface. The third revision implant is configured to be coupled to a first planar surface of the first revision implant.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIGS. 4A-4D illustrate a tibial revision implant component having a planar upper surface, in accordance with some embodiments.

FIGS. 6A-6B illustrate a tibial portion of a total ankle prosthesis having a tibial revision implant component including a stem hole coupled thereto, in accordance with some embodiments.

FIGS. 8A-8B illustrate a tibial portion of a total ankle prosthesis having a tibial revision implant component including a plurality of fastener holes formed therethrough, in accordance with some embodiments.

FIGS. 10 illustrates a talar revision plate, in accordance with some embodiments.

FIGS. 11A-11B illustrate a talar revision plate including a projection, in accordance with some embodiments.

FIGS. 16A-16C illustrate a talar revision plate including a plurality of locking fastener holes formed therethrough, in accordance with some embodiments.

FIG. 20 illustrates a talar revision augment coupled to a talar revision plate, in accordance with some embodiments.

FIGS. 21A-21D illustrate a talar revision dome, in accordance with some embodiments.

DETAILED DESCRIPTION

Figure 1B:
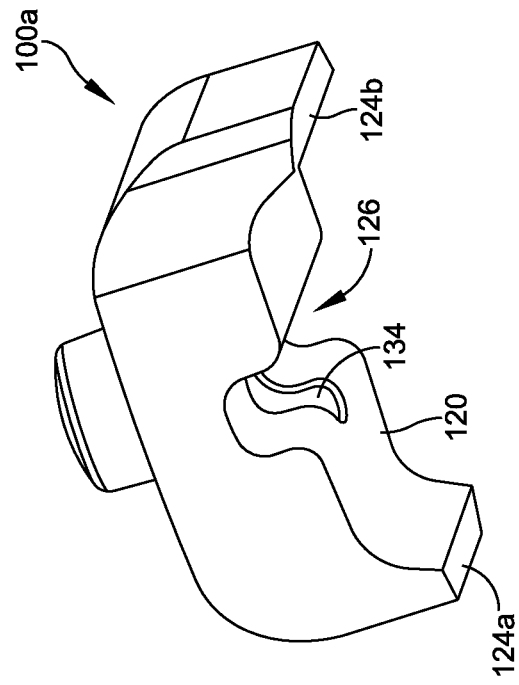
FIGS. 1A-1B illustrate a tibial revision implant component, in accordance with some embodiments.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods advantageously enable revisions of total ankle implants by providing wedges and block designed to be coupled to a primary (or original) total ankle prosthesis component to fill in any gaps and/or voids formed in the bone from osteolysis or during a revision procedure. Although the disclosed systems and methods are described with reference to the INBONE total ankle system available from Wright Medical Technology, Inc., of Arlington, Tenn., the disclosed systems and methods can be adapted for other multi-component prosthesis systems.

Figure 1A:
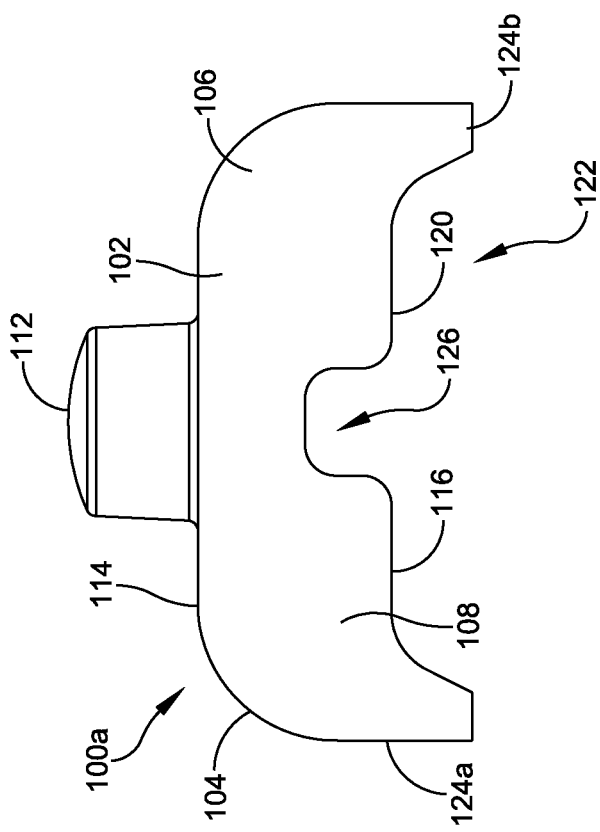

FIGS. 1A and 1B illustrate one example of a revision implant component 100a in accordance with some embodiments. Referring first to FIG. 1A, revision implant component 100a includes a body 102 having an oblong shape including a first side 104, which is curved, and a second side 106, which is also curved and disposed on the opposite side of body 102 as first side 104. A third side 108 is flat and defines a planar surface and is disposed between first and second sides 104 and 106. A fourth side 110 is also flat and defines a planar surface that is disposed opposite third side 108 and between first and second sides 104, 106. Although revision implant component 100a is described as including a plurality of sides 104, 106, 108, 110 that extend between upper side 114 and bottom side 116, revision implant component 100a includes a single side in the form of a circle, oval, or other continuous shape in some embodiments as will be understood by one of ordinary skill in the art.

A head or protection 112 extends from an upper side 114 and is configured to engage a second revision implant component or a modular stem component of an ankle replacement or other prosthesis system. For example, in some embodiments, head 112 is tapered such that it is configured to form a Morse taper with a corresponding recess of another revision implant component or a modular stem component of an ankle replacement or other implant system. In some embodiments, projection 112 is cylindrical, i.e., not tapered, and includes threads, a bayonet coupling, and/or other attachment or coupling means for engaging a complementary feature of another revision implant component or a component of an ankle replacement system. Other coupling means for coupling revision implant component to another revision implant component or a component of a multi-component prosthesis such as, for example, screws, bolts, or other fasteners can also be used.

Figure 4B:
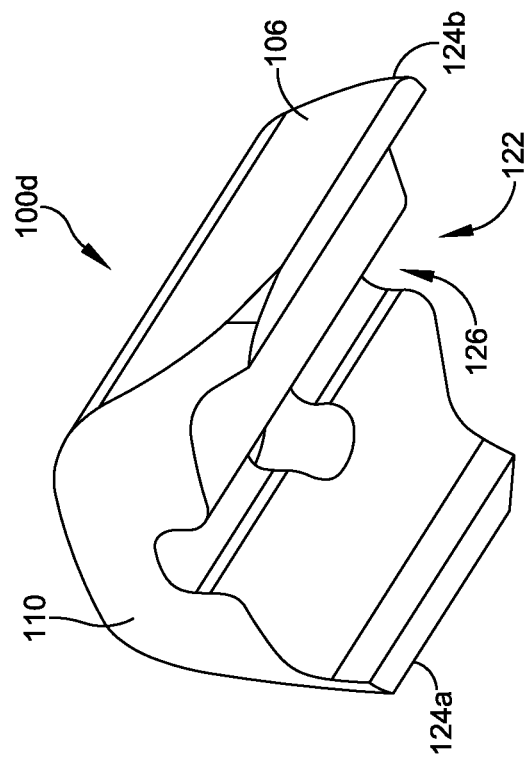
Figure 4A:
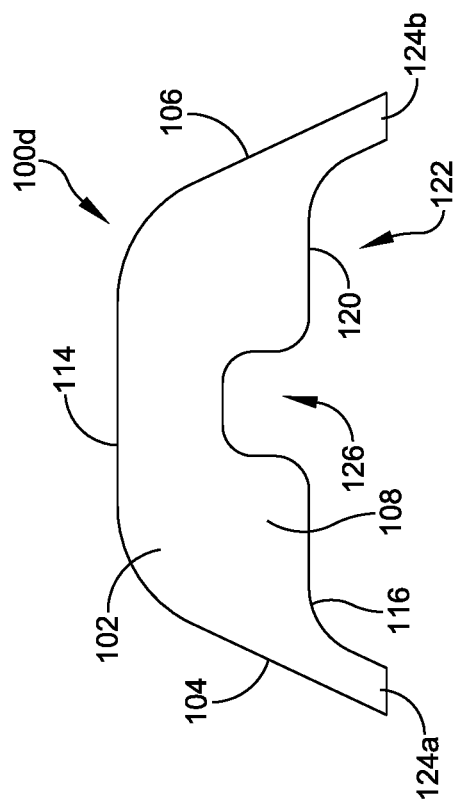

Revision implant component 100a also includes features for coupling and uncoupling the revision implant component 100a from other revision implant components and/or a component of an ankle replacement or other implant system. In some embodiments, the geometry of the revision implant can be complementary to other implant components or to the geometry of intramedullary channels or cavities. The bottom surface 116 of the implant component 100a includes a contoured surface 120 defining a channel 122 that extends inwardly between a first leg 124a and a second leg 124b. The groove 126 extends inwardly from the approximate midpoint of the channel 122 and is sized and configured to receive a raised alignment guide 130 of a tibial platform 132 as best seen in FIG. 4D. The tibial platform 132 is sized and configured to receive an articulating surface (not shown) therein. Examples of tibial platforms are described in U.S. Pat. No. 8,715,362, issued on May 6, 2014 and entitled "Ankle Replacement System," which is hereby incorporated by reference in its entirety. The articulating surface is sized and configured to articulate against a talar articulation surface, such as, for example, the upper surface of a talar dome implant (see, e.g., FIGS. 21A-21D).

Figure 2A:
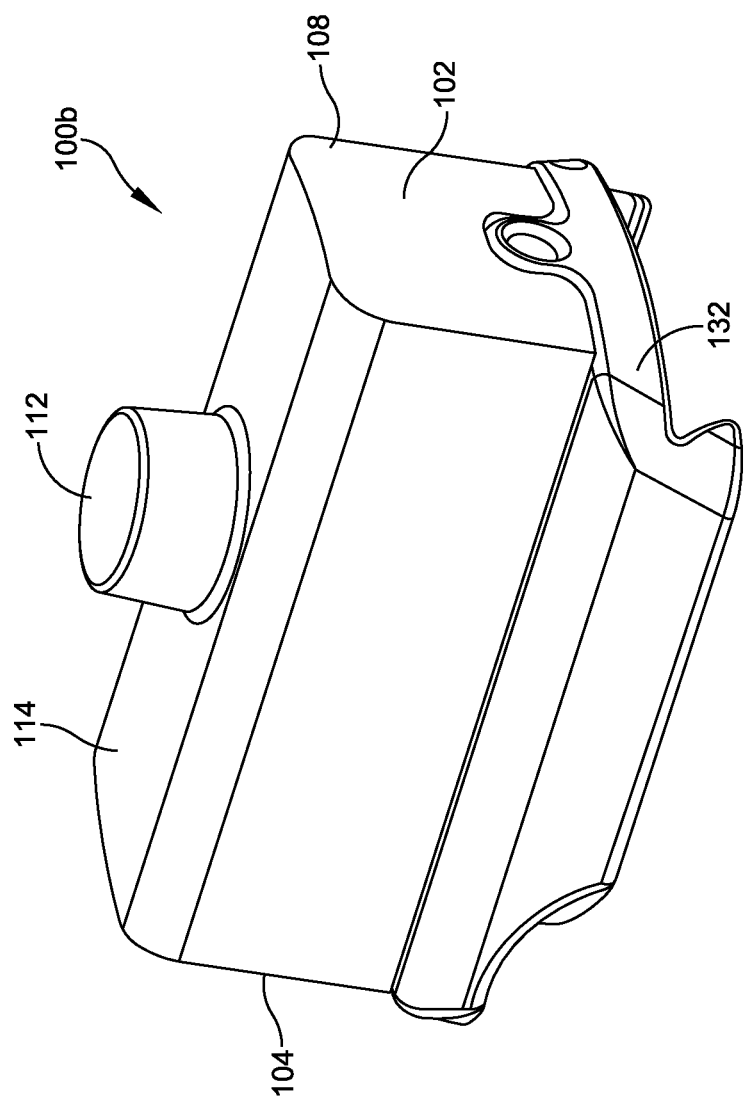
FIGS. 2A-2C illustrate a tibial revision implant component having a generally rectangular shape, in accordance with some embodiments.
Figure 2C:
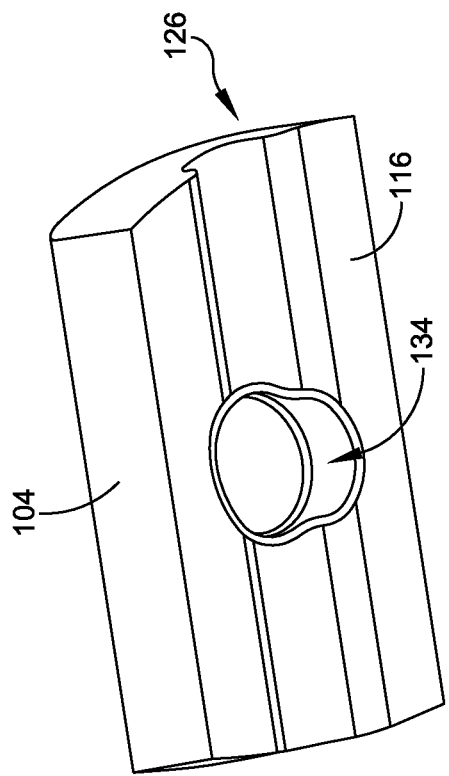
Figure 2B:
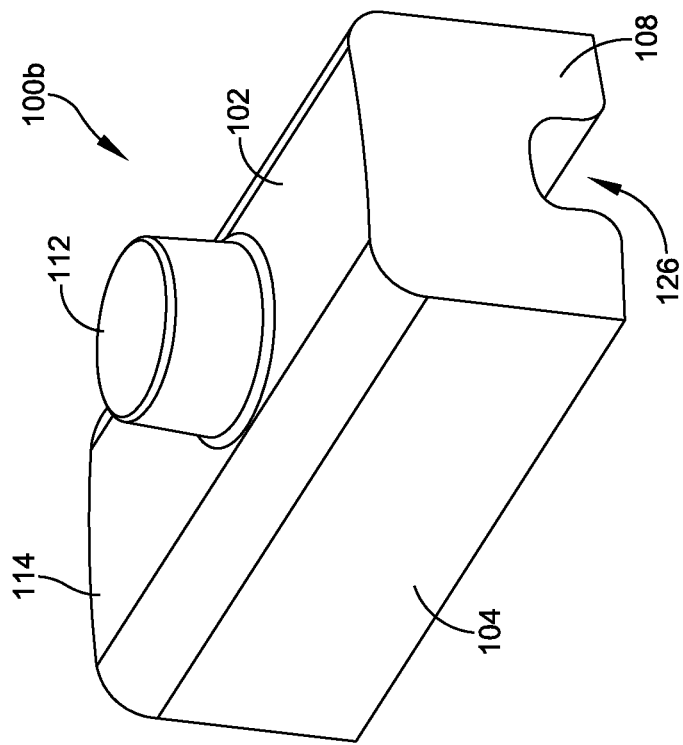

The revision implant component 100a has a predetermined thickness extending from the upper surface 114 to the lower surface 116. The body 102 can have any suitable predetermined thickness, such as, for example, a thickness ranging from 2 mm to 20 mm, such as, for example, 4 mm, 8 mm, 12 mm, 16 mm, and/or any range between 2 mm and 20 mm. In some embodiments, the body 102 has a first predetermined width near a bottom surface 116 and a second predetermined width near a top surface 114. The first predetermined width can be greater than, less than, and/or equal to the second predetermined width. In some embodiments, the second predetermined width is less than the first predetermined width such that the thickness of the body 102 tapers from a bottom surface 116 to a top surface 114. In some embodiments, the predetermined widths are selected to match the width of a primary tibial tray removed during a total ankle revision. For example, in some embodiments, the tibial tray can have a width of 12 mm-30 mm As will be understood by one of ordinary skill in the art, the size and shape of the revision implant components can be varied. For example, FIGS. 2A-2C illustrate another embodiment of a tibial tray revision implant 100b. The tibial tray revision implant 100b includes a body 102 having a generally rectangular shape. The sides 104-110 are substantially flat and each define a substantially planar surface. The interfaces between adjacent sides 104-110, 114, 116 can be rounded, although one of ordinary skill in the art will understand that the interfaces can be pointed and/or chamfered. The tibial tray revision implant 100b is similar to the tibial tray revision implant 100a described in conjunction with FIGS. 1A-1B, and similar description is not repeated herein.

The bottom surface 116 of the tibial tray revision implant 100b defines a generally planar surface having a groove 126 formed therein. The groove 126 extends inwardly from the approximate midpoint of each of the side walls 108, 110 and is sized and configured to receive a raised alignment guide 130 of a tibial platform 132, as shown in FIG. 2A. A hole 134 extends from the groove 126 into the body 102. In some embodiments, the hole 134 is located at an approximate mid-point of the body 102, although it will be appreciated that the hole 134 can extend into the body 102 from any point within the groove 126. The holes 134 is sized and configured to receive a fastener therein. The fastener couples the revision implant 100*b* to one or more other revision implant components and/or primary components of a multi-component prosthesis.

Figure 3A:
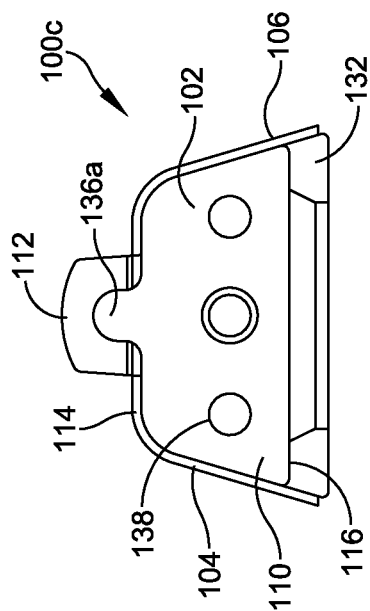
FIGS. 3A-3C illustrates a tibial revision implant component including a plurality of longitudinal protrusions, in accordance with some embodiments.
Figure 3B:
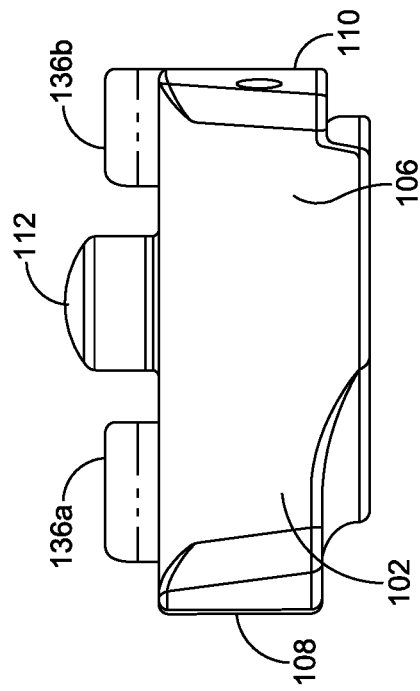
Figure 3C:
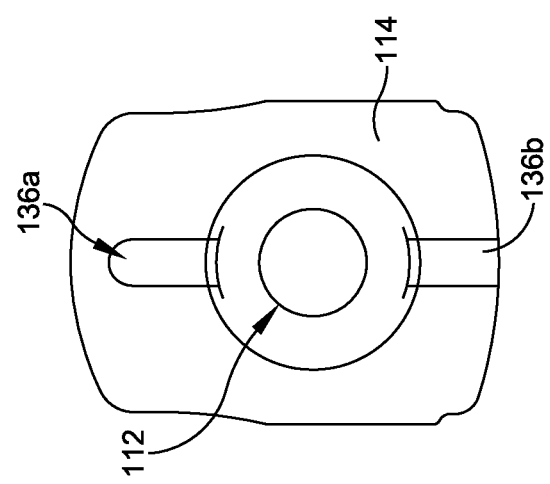

FIGS. 3A-3C illustrate another embodiment of a tibial tray revision implant 100*c*. The tibial tray revision 100*c* includes a body 102 defined by walls 104, 106, 108, and 110. The side walls 104, 106 are tapered from a bottom surface 116 to a top surface 114. In some embodiments, the walls 108, 110 define planar surfaces extending perpendicular to the bottom surface 116 and/or the top surface 114. The tibial tray revision 100*c* is similar to the tibial tray revision 100*a* described in conjunction with FIGS. 1A-1B, and similar description is not repeated herein. In some embodiments, the tibial tray revision 100*c* can have an increased thickness to accommodate additional bone removal during a revision procedure, although it will be appreciated that the tibial tray revision 100*c* can have an increased, decreased, and/or constant thickness as compared to a tibial tray installed during a previous total ankle replacement and/or revision procedure.

As illustrated in FIGS. 3A-3B, the tibial tray revision implant 100*c* includes a plurality of longitudinal protrusions 136*a*, 136*b* that extend from an upper surface 114 of the body 102. The longitudinal protrusions 136*a*, 136*b* can be located on either side of the head 112. The longitudinal protrusions 136*a*, 136*b* extend along any portion of the upper surface 114. For example, in the illustrated embodiment, the longitudinal protrusions 136*a*, 136*b* are centered with respect to the side walls 108, 110 and extend at least partially from the side walls 108, 110 towards the head 112. FIG. 3C illustrates a top-down view of upper surface 114.

In some embodiments, the tibial tray revision implant 100*c* includes a bottom surface 116 is configured to interact with a top surface of a tibial insert (not shown). The bottom surface 116 can have a rounded and/or squared surface configured to match the geometry of the a tibial insert. In some embodiments, the bottom surface 116 can include one or more projections, extensions, grooves, and/or insets configured to interact with one or more features of a tibial insert.

FIGS. 4A-4D illustrate another embodiment of a tibial tray revision implant 100*d*. The tibial tray revision implant 100*d* includes a body 102 having side walls 104, 106, 108, 110. The tibial tray revision implant 100*d* is similar to the tibial tray revision implant 100*a* described above with respect to FIGS. 1A-1B, and similar description is not repeated herein. The tibial tray revision implant 100*d* omits the head 112 and includes a planar upper surface 114. The planar upper surface 114 is configured to couple to one or more components of a total ankle prosthesis and/or one or more revision implants. In some embodiments, a fastener hole (not shown) extends through the body 102 of the tibial tray revision implant 100*d*.

Figure 4C:
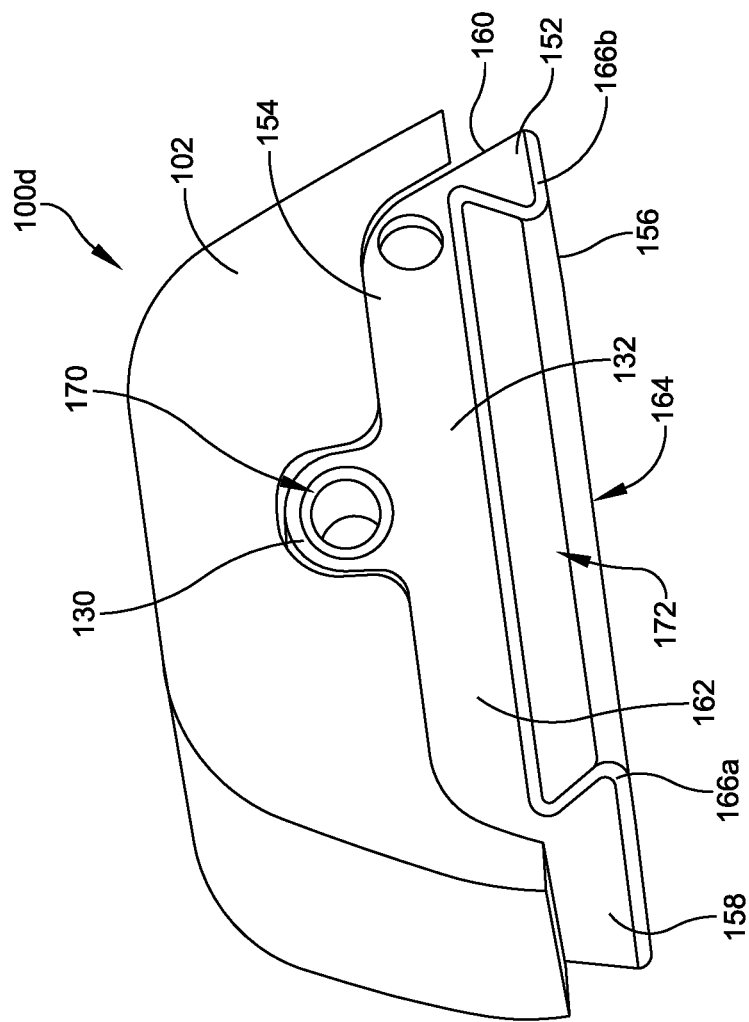

FIG. 4C illustrates one embodiment of a tibial tray revision implant 100*d* having a tibial platform 132 coupled thereto. The tibial platform 132 includes a body 152 extending between an upper surface 154 and a lower surface 156. The tibial tray 150 includes side walls 158, 160, a front wall 162, and a back wall 164. The side walls 158, 160 and the back wall 164 define a slot 172 for receiving an articulation component (not shown) therein. In some embodiments, the side walls 158, 160 define retaining legs 166*a*, 166*b* having a tapered inner wall 174 configured to retain the articulation component therein.

The upper surface 154 of the tibial platform 132 includes a contoured surface sized and configured to mate with the contoured lower surface 116 of the tibial revision implant 100*d*. In some embodiments, the tibial platform 132 includes a raised alignment guide 130. The raised alignment guide 130 is sized and configured to fit within the groove 126 formed in the bottom surface 116 of the tibial revision implant 100*d*. The raised alignment guide 130 and the groove cooperate to position the tibial platform 132 in a predetermined position with respect to the tibial revision implant 100*d*. In some embodiments, the raised alignment guide 130 extends longitudinally from the front wall 162 towards a center point of the body 152. In other embodiments, the raised alignment guide 130 has a length configured to match the length of the groove 126.

As shown in FIG. 4D, in some embodiments, a head 168 extends from an upper surface 154 of the tibial platform 132. The head 168 is sized and configured to mate with the head opening 134 defined by the tibial tray revision implant 100*d*. The head 168 can define a fastener hole (not shown) that is concentric with a fastener hole 140 formed through the tibial tray revision implant 100*d*. In some embodiments, the raised alignment guide 130 and the head 168 provide a fixed engagement position of the tibial platform 130 with respect to the tibial tray revision implant 100*d*. In some embodiments, the head 168 has the same length and circumference as the head 112 formed on the tibial tray revision implant 100*a*.

Figure 5:
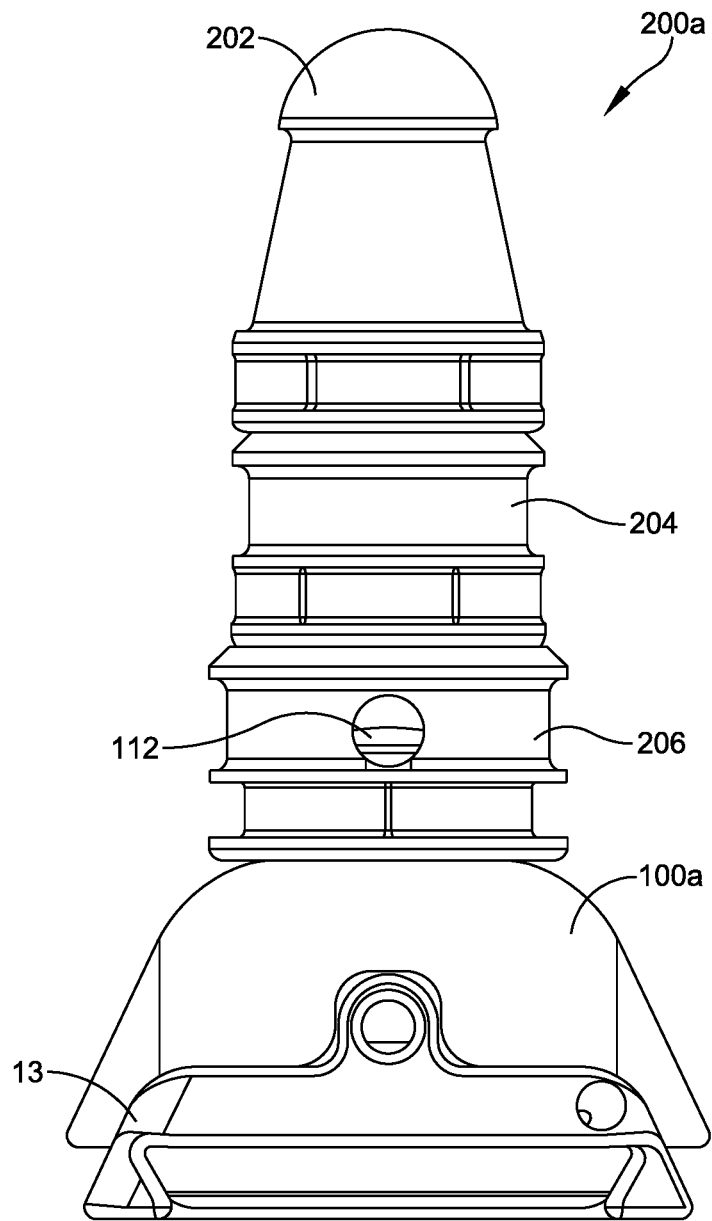
FIG. 5 illustrates a tibial portion of a total ankle prosthesis having a tibial revision implant component coupled thereto, in accordance with some embodiments.

FIG. 5 illustrates one embodiment of a tibial portion 200*a* of a total ankle prosthesis having a tibial tray revision implant 100*a* coupled thereto. The tibial portion 200*a* includes a stem 202 having one or more stem components 204, 206. The tibial revision implant 100*a* is coupled to the bottom stem component 206. For example, in some embodiments, the head 112 is inserted into a hole formed in a bottom surface of the stem 202 (not shown). The tibial revision implant 100*a* increases the spacing between the stem 202 and the tibial platform 132 to fill a bone void formed in the ankle joint.

FIGS. 6A-6B illustrate another embodiment of a tibial portion 200*b* of a total ankle prosthesis having a tibial tray revision implant 100*d* coupled thereto. The tibial portion 200*b* is similar to the tibial portion described in conjunction with FIG. 5 and similar description is not repeated herein. The tibial tray revision implant 100*d* defines a stem hole extending from an upper surface 116 through the body 102 to the lower surface 114. The stem hole is sized and configured to receive a portion of the stem 202 therein. The stem hole is further sized and configured to receive a head 168 of a tibial platform 132 therein. The head 168 of the tibial platform 132 is configured to mate with a bottom portion 206 of the stem 202. When the tibial platform 132 is coupled to the stem 202, the revision implant 100*d* and the tibial platform 132 are maintained in a fixed position with respect to the stem 202.

Figure 7:
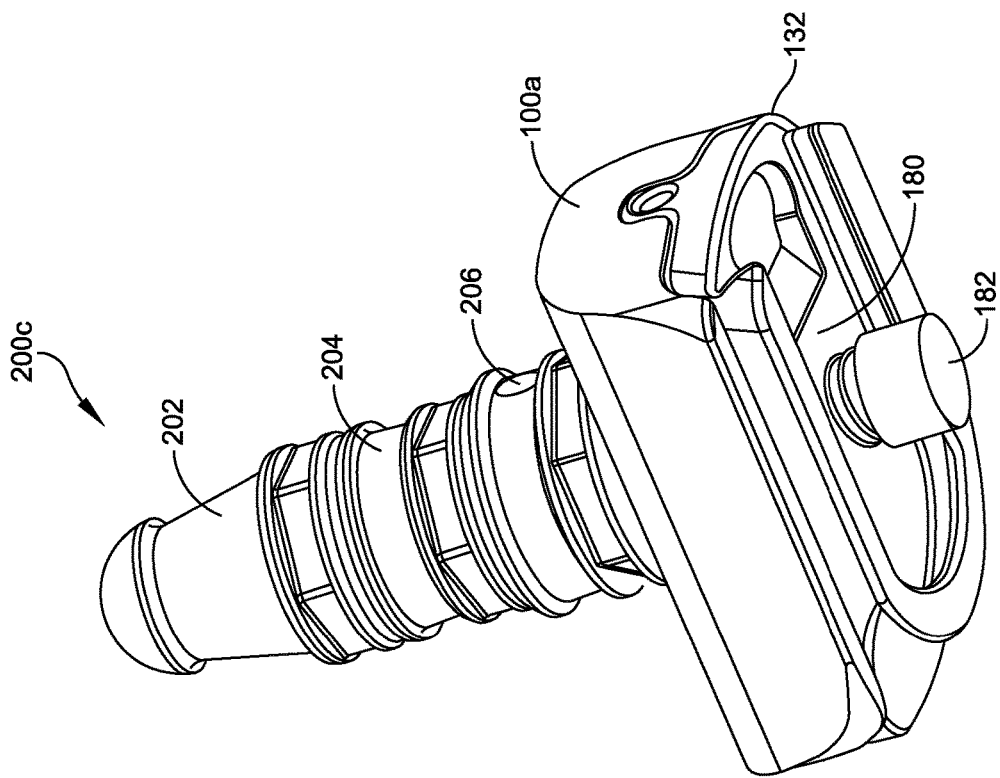
FIG. 7 illustrates a tibial portion of a total ankle prosthesis having a tibial revision implant component including a fastener hole formed therethrough, in accordance with some embodiments.

FIG. 7 illustrates another embodiment of a tibial portion 200*c* of a total ankle prosthesis having a tibial tray revision 100*a* coupled thereto. The tibial portion 200*c* is similar to the tibial portion described in conjunction with FIG. 5, and similar description is not repeated herein. The tibial platform 132 includes a fastener hole 180 extending from an upper surface 154 through the body 152 to a lower surface 156.

The fastener hole 180 is sized and configured to receive a fastener 182 therein. The fastener 182 extends through the fastener hole 180 and can extend into one or more fastener holes 140 formed in the tibial tray revision 100a. In some embodiments, the fastener 182 extends through the tibial tray revision 100a and mates with a fastener hole formed in a bottom portion 206 of the stem 202.

Figure 8B:
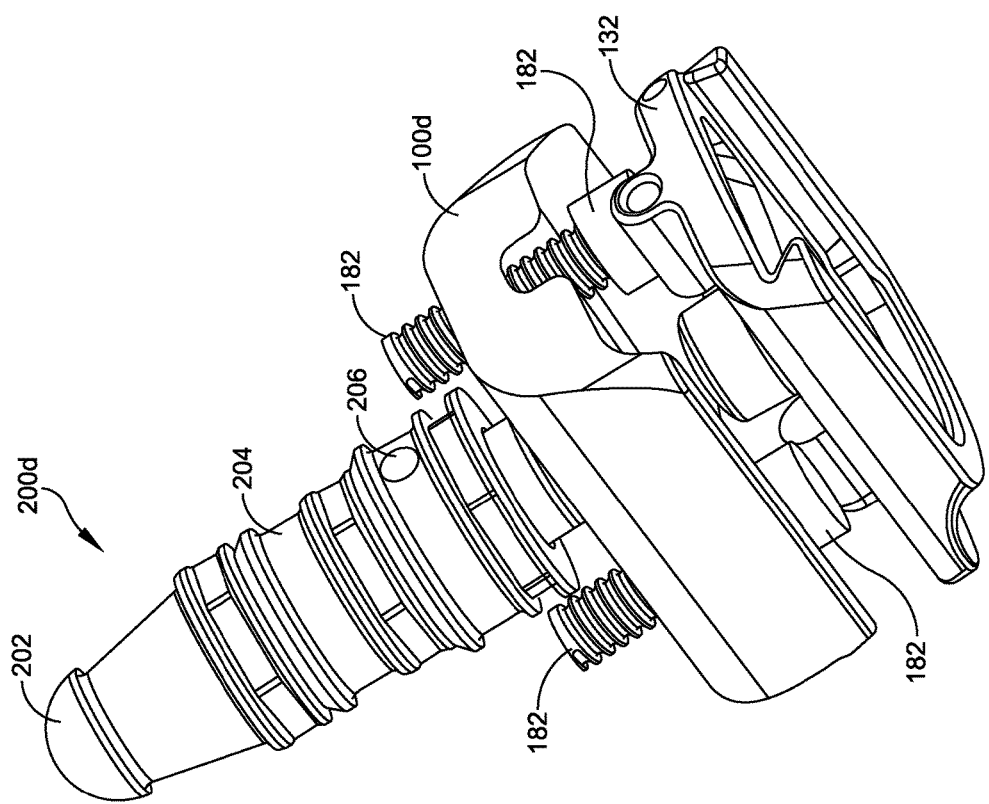

FIGS. 8A-8B illustrate another embodiments of a tibial portion 200d of a total ankle prosthesis having a tibial tray revision 100d coupled thereto. The tibial portion 200c is similar to the tibial portion 200a described in conjunction with FIG. 5, and similar description is not repeated herein. The tibial platform 132 includes two fastener holes 180a, 180b extending from an upper surface 154 through the body 152 to the lower surface 156. The fastener holes 180a, 180b are sized and configured to receive fasteners 182 therethrough. The fasteners 182 extend through the fastener holes 180a, 180b and anchor the tibial platform 132 to the tibial tray revision implant 100d. In some embodiments, the fasteners 182 extend through the tibial tray revision implant 100d such that a first end of the fastener 182 extends at least partially above the upper surface 114 of the tibial tray revision implant 100d.

Figure 9A:
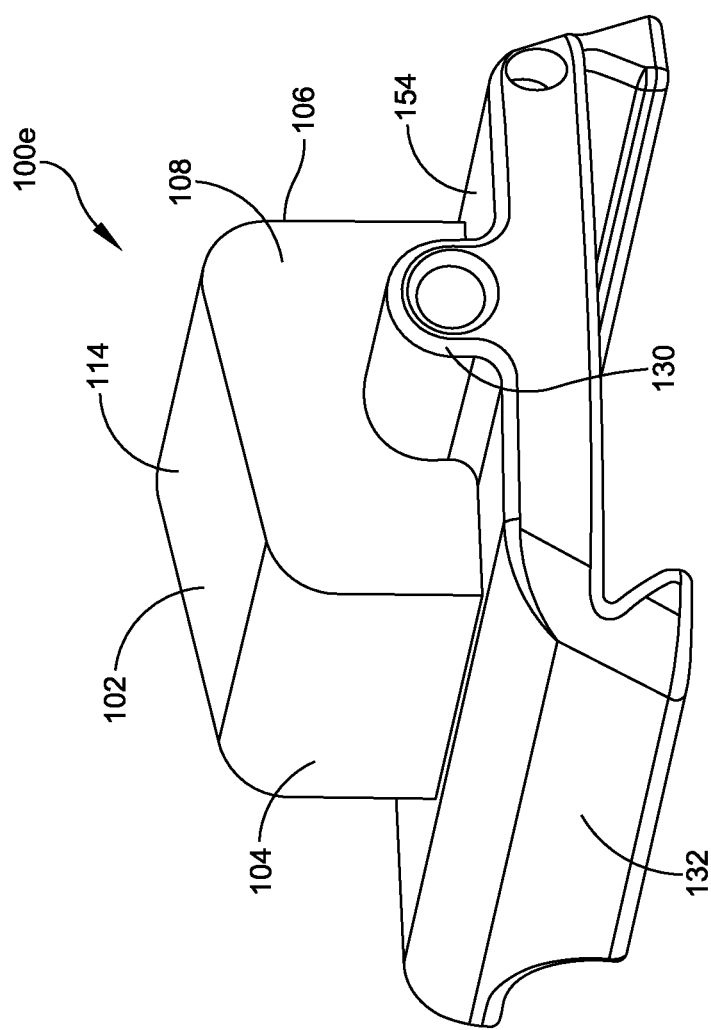
FIGS. 9A-9B illustrate a tibial revision implant component including a body having a perimeter less than the width of an upper surface of a tibial platform, in accordance with some embodiments.
Figure 9B:
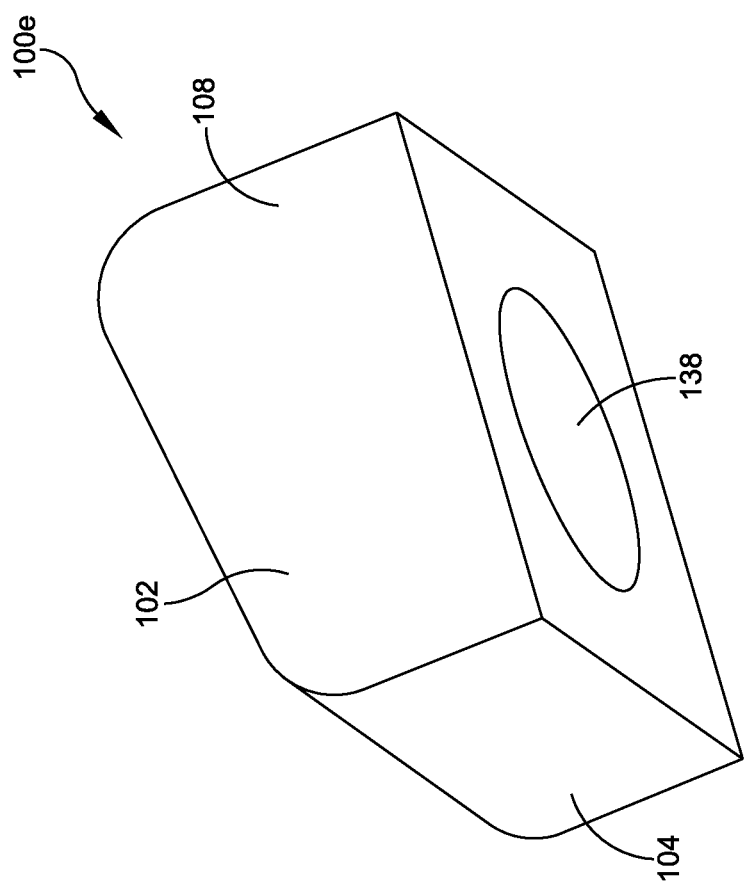

FIGS. 9A-9B illustrate one embodiment of a tibial tray revision implant 100e having a body 102 defined by side walls 104, 106, 108, 110. The revision implant 100e is similar to the revision implant 100a described in conjunction with FIGS. 1A-1B, and similar description is not repeated herein. The bottom surface 116 of the revision implant 100e defines a head opening 138 sized and configured to receive a head 168 of a tibial platform 132 therein. The body 102 defines a perimeter having a width less than the width of an upper surface 154 of the tibial platform 132. In some embodiments, at least one side wall 108 abuts an alignment guide 130 formed on the upper surface 154 of the tibial platform 132. In some embodiments, the top surface 114 of the tibial tray revision implant 100e is slanted from a first side wall 104 to a second side wall 106.

In some embodiments, a total ankle revision includes revision and/or replacement of a talar prosthesis. FIG. 10 illustrates one embodiment of talar revision plate 300a. The talar revision plate 300a includes a body 302 having a predetermined thickness extending between a upper surface 304 and a lower surface 306. The upper and lower surfaces 304, 306 generally define planar surfaces. A side wall 308 extends about a perimeter of the body 302. In some embodiments, the revision plate 300a includes a head 312 extending from the upper surface 304 of the body 302. The head 312 is sized and configured to couple a talar dome (or other talar prosthesis) to the revision plate 300a. In some embodiments, the head 312 has a cylindrical shape and extends a predetermined height above the upper surface 304. A removal feature 314 can extend through an upper portion of the head 312 to allow for removal of the revision plate 300a during the same and/or subsequent revision procedures. In some embodiments, the head 312 defines a fastener hole 316 extending from a top surface at least partially into the head 312 and/or the body 302.

In some embodiments, one or more protrusions 320 (or stems) extend from the bottom surface 306 of the revision plate 300a. The one or more protrusions 320 are sized and configured to anchor the revision plate 300a to a resected talus. The protrusions 320 extend a predetermined length and at a predetermined angle from the bottom surface 306 and have a rounded distal end 324. For example, in some embodiments, one or more stems 320 extend from the bottom surface 306 at a predetermined angle between 5-90°, such as, for example, 5, 10, 15°, 30°, 45°, 60°, 75°, 90°, and/or any other suitable angle. The revision plate 300a can include any suitable number of stems, such as, for example, one stem, two stems, there stems, four stems, and/or any other number of stems.

Figure 11A:
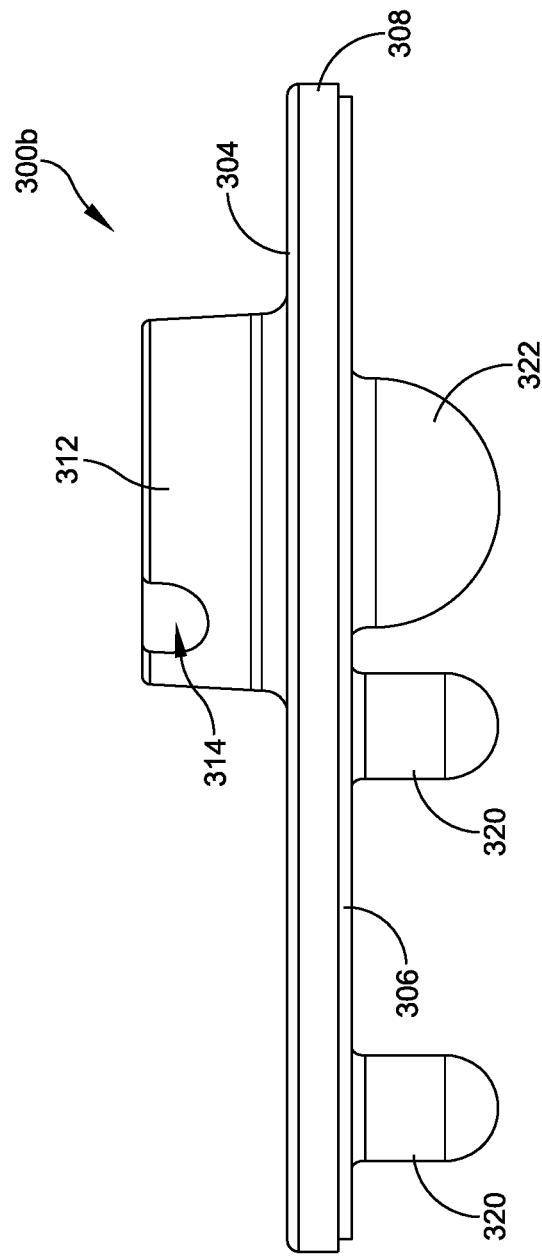

FIGS. 11A-11B illustrate another embodiment of a talar revision plate 300b having a projection feature 322 extending therefrom. The talar revision plate 300b is similar to the talar revision plate 300a described in conjunction with FIG. 10, and similar description is not repeated herein. The talar revision plate 300b includes a projection feature 322 extending from a bottom surface 306 of the plate 300b.

Figure 12:
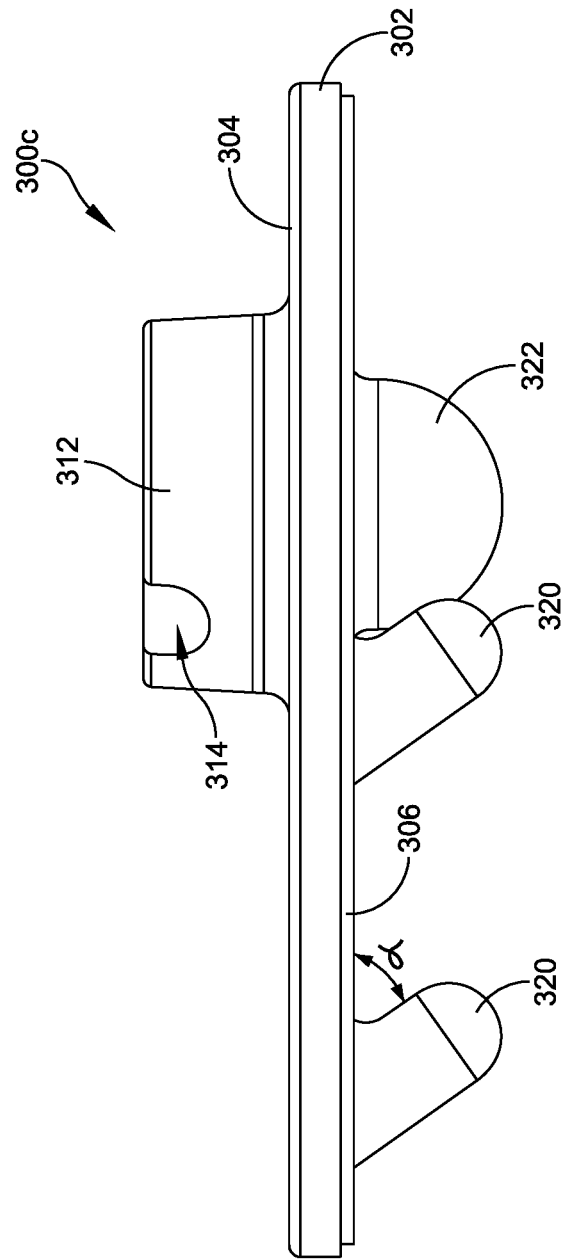
FIG. 12 illustrates a talar revision plate including a plurality of stems extending from a bottom surface, in accordance with some embodiments.

FIG. 12 illustrates another embodiment of a talar revision plate 300c. The talar revision plate 300c is similar to the talar revision plate 300b described in conjunction with FIGS. 11A-11B, and similar description is not repeated herein. The talar revision plate 300c includes a plurality of stems 320 extending from the bottom surface 306 at a predetermined angle α. The predetermined angle α be any suitable angle, such as, for example, an angle between 5-90°, such as, for example, 5, 10, 15°, 30°, 45°, 60°, 75°, 90°, and/or any other suitable angle. Tangle α between each of the stems 320 and the revision plate 300c can be the same and/or can vary between each of the stems 320.

Figure 13:
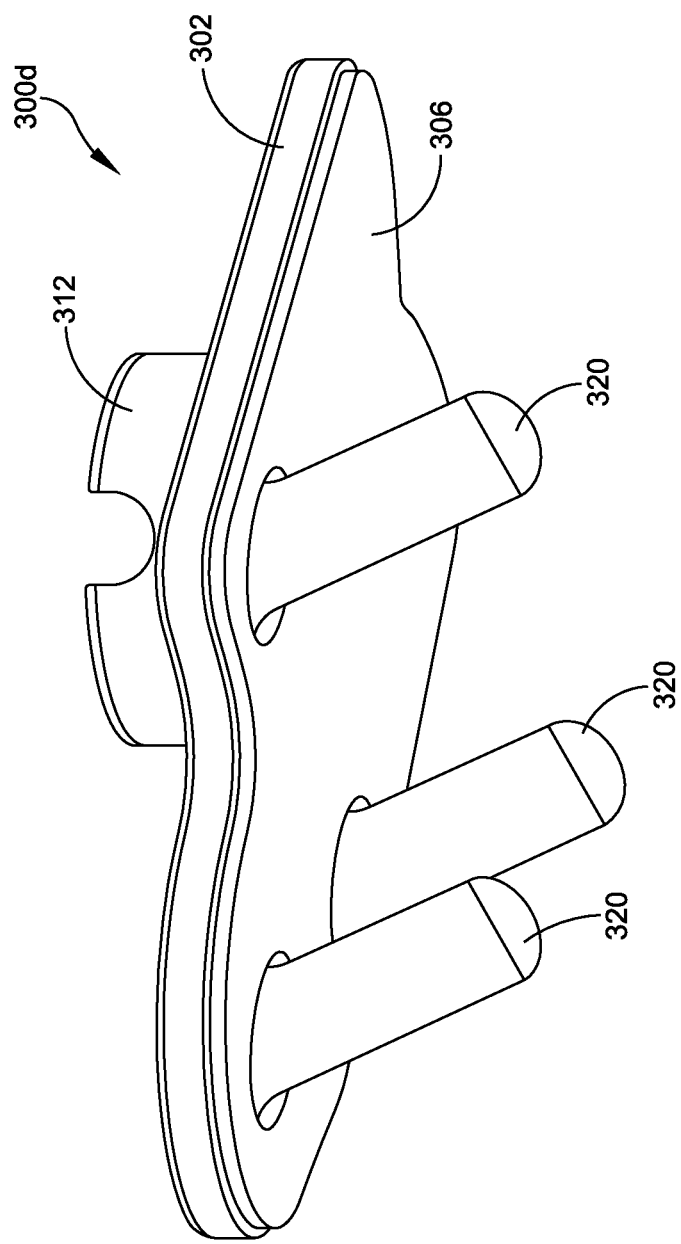
FIG. 13 illustrates a talar revision plate including a plurality of stems extending from a bottom surface at a predetermined angle, in accordance with some embodiments.

FIG. 13 illustrates one embodiment of a talar revision plate 300d. The talar revision plate 300d is similar to the talar revision plate 300c described in conjunction with FIG. 12, and similar description is not repeated herein. The talar revision plate 300d includes a plurality of stems 320 extending from the bottom surface 306 at a predetermined angle α. The talar revision plate 300d has a planar bottom surface 306 that omits the projection 322. The planar bottom surface 306 is sized and configured to couple to a resected talar bone. The one or more stems 320 extend into the talar bone and maintain the plate 300d in a fixed position. In some embodiments, a fastener hole (not shown) extends through the head 312 and extends through the lower surface 306.

Figure 14:
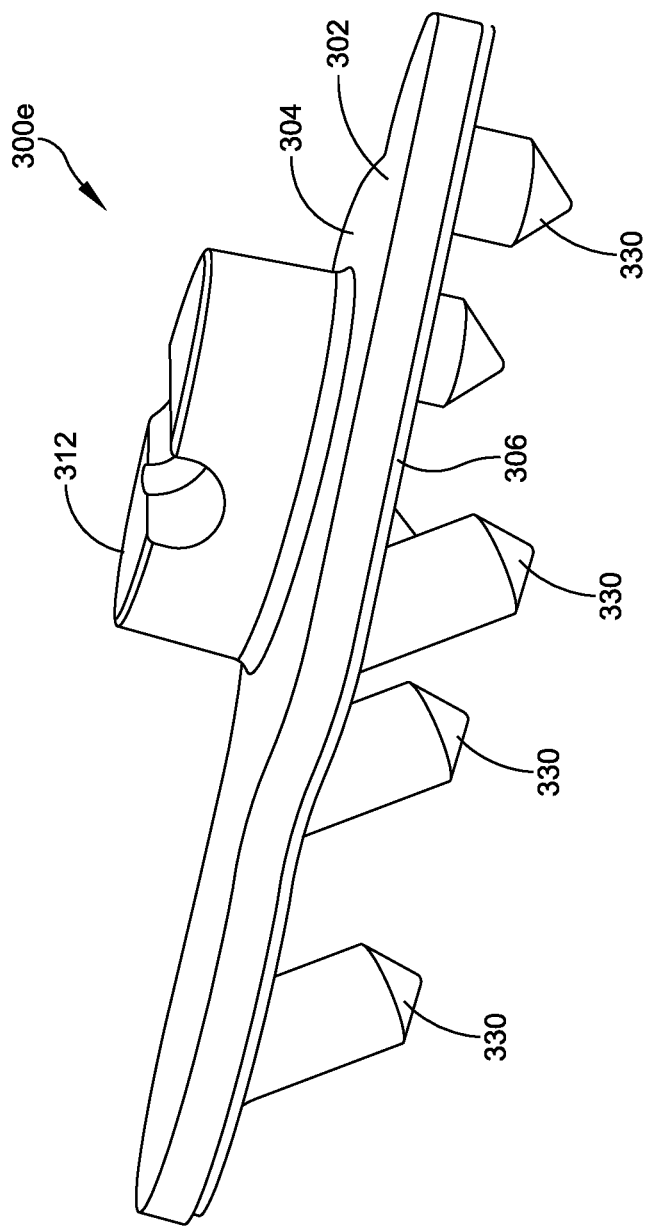
FIG. 14 illustrates a talar revision plate including a plurality of spikes extending from a bottom surface at a predetermined angle, in accordance with some embodiments.

FIG. 14 illustrates one embodiment of a talar revision plate 300e. The talar revision plate 300e is similar to the talar revision plate 300a described above in conjunction with FIGS. 11A-11B, and similar description is not repeated herein. The talar revision plate 300e includes a plurality of spikes 330 extending from the bottom surface 306 of the plate 300e. The spikes 330 are similar to the stems 320 described above. but have pointed and/or sharpened ends 332. The pointed ends 332 of the spikes 330 are driven into the talus to maintain the talar revision plate 300e in a fixed position with respect to the talus. The spikes 330 can extend from the bottom surface 306 of the plate 300e at a predetermined angle, such as, for example, 5, 10, 15°, 30°, 45°, 60°, 75°, 90°, and/or any other suitable angle. The talar revision plate 300e can include any suitable number of spikes 330, such as, one spike, two spikes, three spikes, six spikes, and/or any other suitable number of spikes.

Figure 15A:
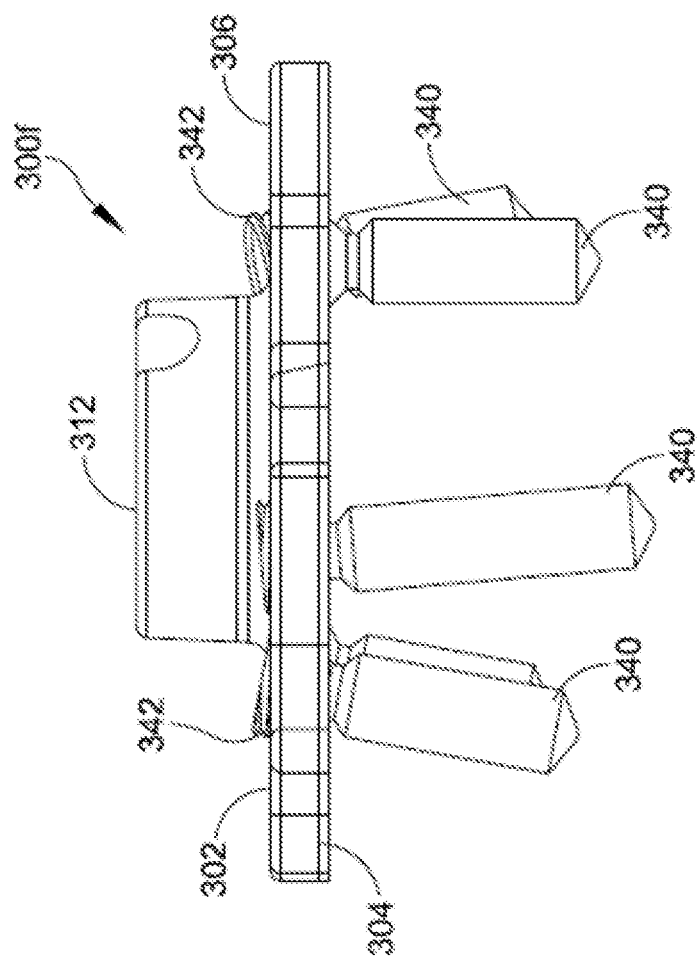
FIG. 15A illustrates a talar revision plate including a plurality of variable angle pegs, in accordance with some embodiments.
Figure 15B:
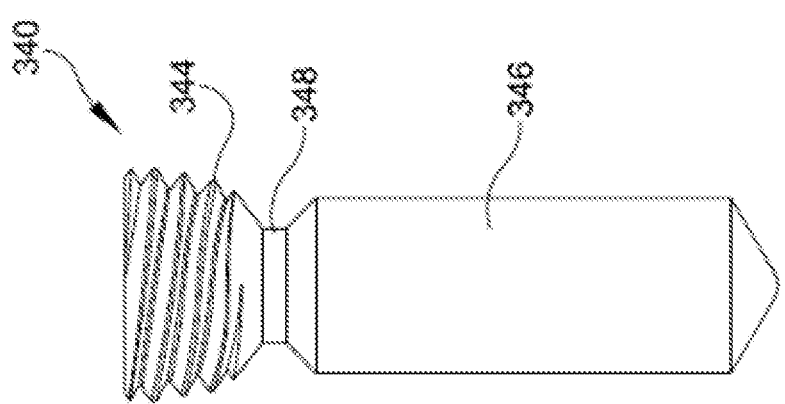
FIG. 15B illustrates a variable angle peg, in accordance with some embodiments.

FIG. 15A illustrates one embodiment of a talar revision plate 300f including a plurality of variable angle pegs 340. The talar revision plate 300f is similar to the talar revision plate 300a described in conjunction with FIG. 10, and similar description is not repeated herein. The talar revision plate 300f includes a plurality of peg holes 342 formed from the top surface 304 through the bottom surface 306. A plurality of variable angle pegs 340 are sized and configured to be inserted through the peg holes 342, as shown in FIG. 15B. The variable angle pegs 340 include a threaded head 344 and a peg body 346 extending longitudinally from the threaded head 344. The peg body 346 can extend a predetermined length sufficient to anchor the talar revision plate 300f to a talus.

In some embodiments, the peg holes 342 include an inner surface configured to allow insertion of the variable angle pegs 340 at a selected angle within a predetermined range of angles. For example, in some embodiments, the inner surface of the peg holes 340 includes one or more threads, partial threads, projections, and/or metal mesh configured to mate with the threaded head 344 of the variable angle pegs 340. In other embodiments, the inner surface of the peg holes 340 includes a smooth surface configured to be tapped by the threaded head 344. The variable angle peg holes 340 can be inserted at any angle selected within a predetermined range of angles, such as, for example, between 15-90°, such as, for example, 15°, 30°, 45°, 60°, 75°, 90°, and/or any other suitable angle. The angle between the variable angle peg 340 and the plate 300f can be selected by a surgeon during a revision procedure.

Figure 16A:
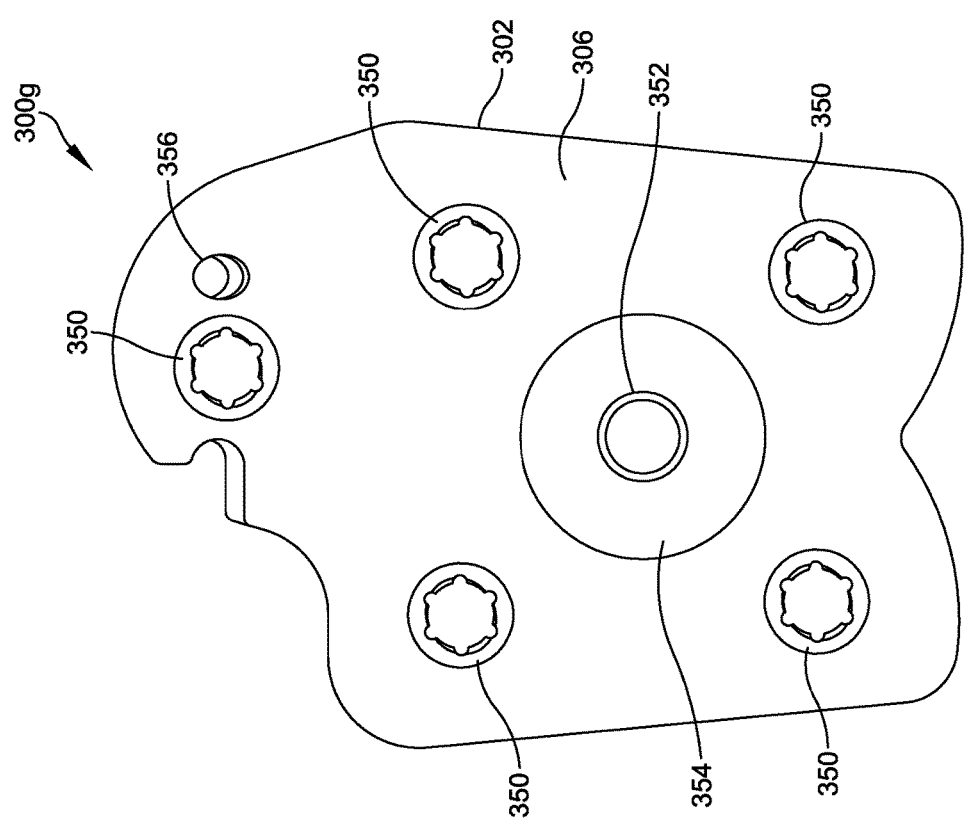
Figure 17A:
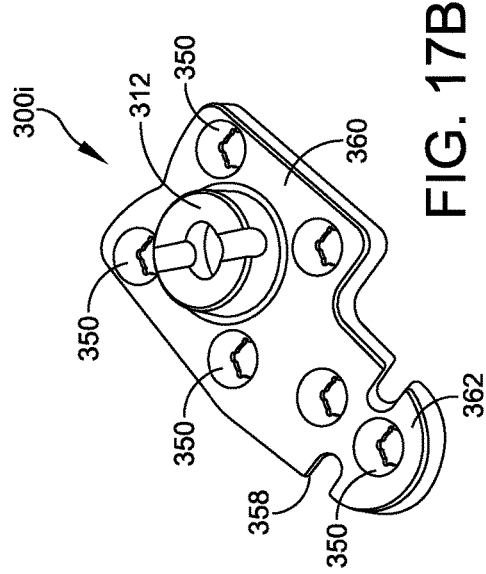
FIGS. 17A-17H illustrate various talar revision plates having a talar portion and a calcaneal portion, in accordance with some embodiments.
Figure 17B:
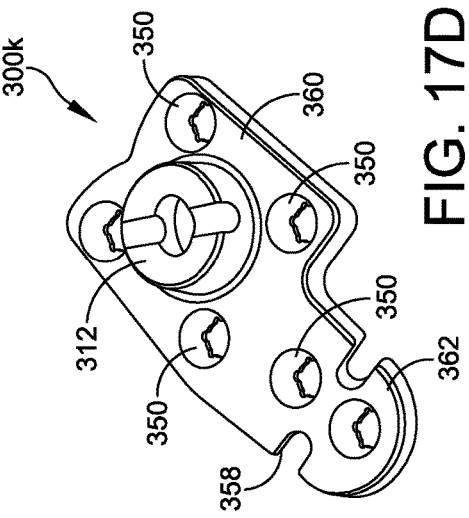
Figure 17C:
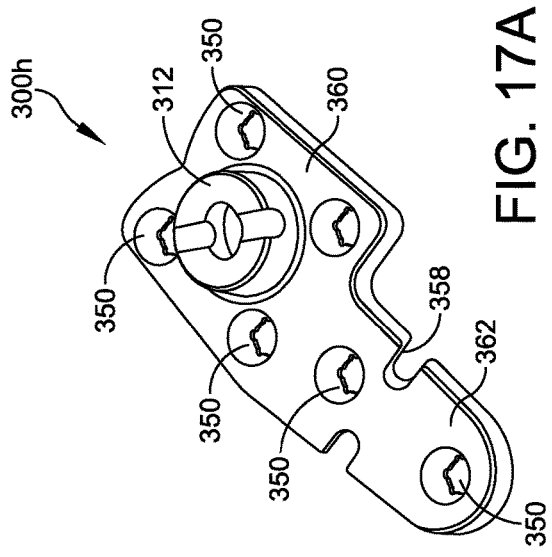
Figure 17D:
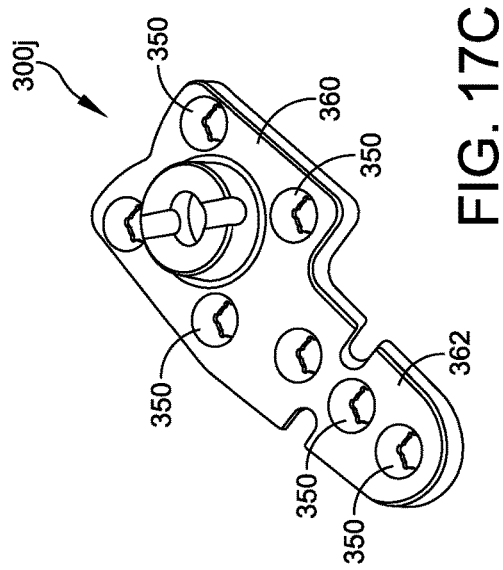
Figure 17E:
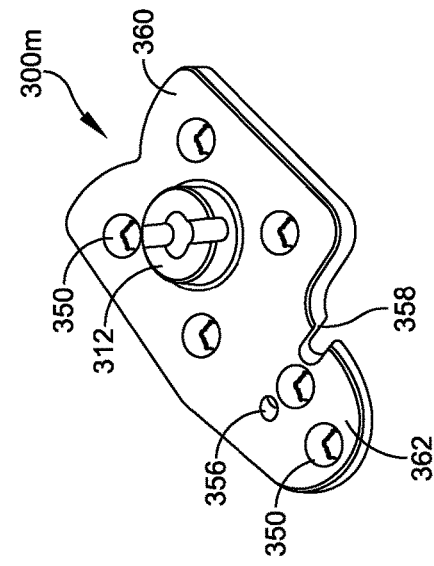
Figure 17F:
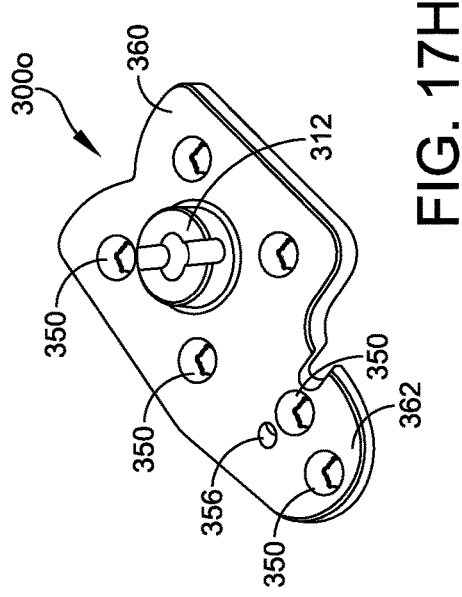
Figure 17G:
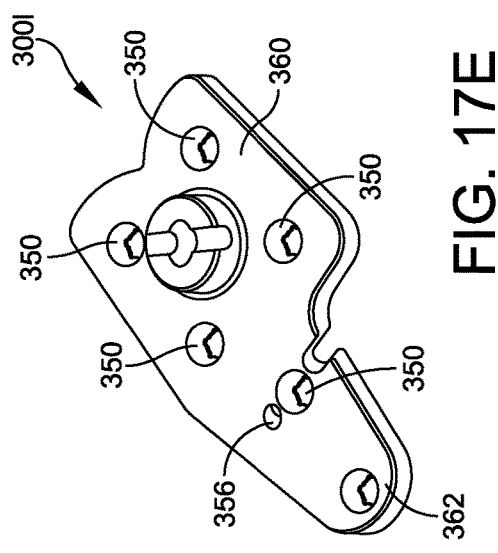
Figure 17H:
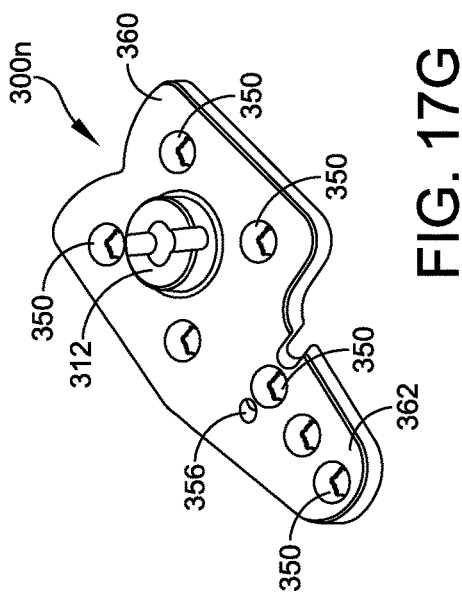

FIGS. 16A-16C illustrate one embodiment of a talar revision plate 300g having a plurality of fastener holes 350 formed therethrough. The talar revision plate 300g is similar to the talar revision plate 300d described in conjunction with FIG. 13 above, and similar description is not repeated herein. The talar revision plate 300g includes a plurality of fastener holes 350 extending from the upper surface 304 through the lower surface 306. The plurality of fastener holes 350 can include locking and/or non-locking fastener holes 350. For example, in some embodiments, one or more fastener holes 350 are configured to receive an Ortholoc 3Di locking screw available from Wright Medical, Memphis, Tenn. The fastener holes 350 can comprise any suitable locking and/or non-locking engagement.

In some embodiments, an alignment feature 352 extends from an upper surface of the head 312 to the lower surface 306 of the body 302. The alignment feature 352 is sized and configured to receive a complimentary alignment feature of one or more other revision elements therein. The alignment feature 352 can be configured to interface with any suitable alignment feature, such as, a protrusion, a groove, an inset, and/or any other suitable alignment feature formed on talar prosthesis and/or additional elements of a total ankle replacement and/or revision.

FIGS. 17A-17H illustrate various embodiments of talar revision plates 300h-300o. The talar revision plates 300h-300o are similar to the talar revision plate 300a described in conjunction with FIG. 10, and similar description is not repeated herein. As shown in FIGS. 17A-17H, the talar revision plates 300h-300o can include a first portion 360 and a second portion 362. The first portion 360 is sized and configured to be coupled to a first bone, such as a resected talus, during a revision procedure. The first portion 360 can include a plurality of fastener holes 350 therethrough. The first portion 360 can have various sizes, thicknesses, and/or other parameters sized and configured to fit various sized talar resections. In some embodiments, the first portion 360 defines a generally rectangular and/or oval shape.

In some embodiments, the talar revision plates 300h-300o include a second portion 362 sized and configured to extend over a second bone, such as, for example, a navicular, when the talar revision plate 300h-300o is coupled to a talus during a revision procedure. The second portion 362 extends a first side 364 of the first portion 360 and can have a substantially rounded or horn-shape. The second portion 362 is sized and configured to bridge a talar-navicular joint. In some embodiments, the second portion 362 includes a plurality of fastener holes 350 sized and configured to attach the second portion 362 to a talus and/or navicular bone. The first portion 360 and/or the second portion 362 of the talar plate revision plates 300h-300o can include any number of fastener holes 350, such as, for example, one, two, three, four, or more fastener holes 350. The fastener holes 350 can include locking, non-locking, polyaxially locking, and/or compression slots. In some embodiments, the second portion 362 includes at least one compression fastener 356 hole configured to receive a compression screw therein that passes from the navicular into the talus to provide additional fusion of the talar-navicular joint.

Figure 18A:
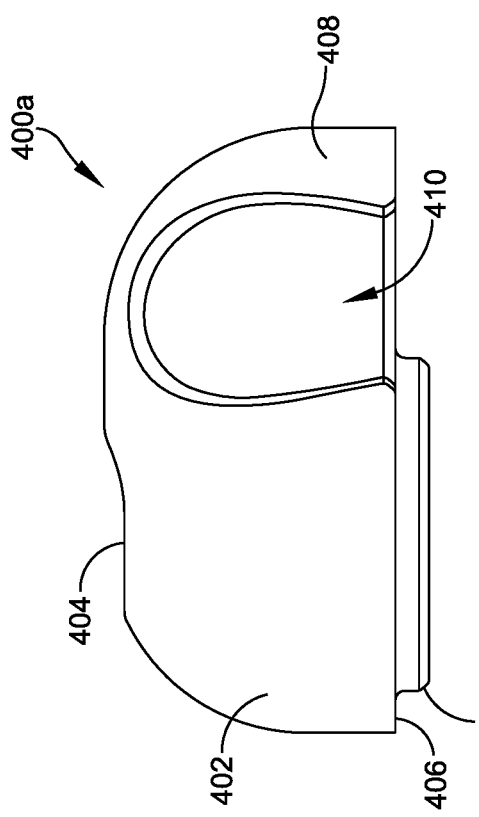
FIGS. 18A-18C illustrate a talar revision augment, in accordance with some embodiments.
Figure 18B:
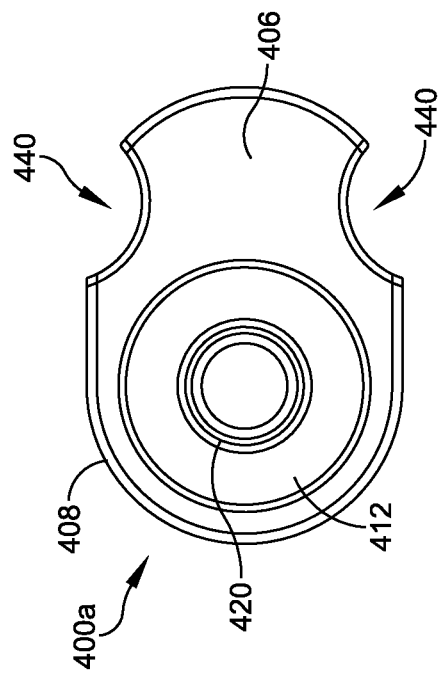

In some embodiments, a total ankle revision includes a talar revision augment. FIGS. 18A-18B illustrate one embodiment of a talar revision augment 400a, The talar revision augment 400a includes a body 402 extending between an upper surface 404 and a lower surface 406. A side wall 408 extends about a perimeter of the body 402. The side wall 408 and the upper surface 406 can define a rounded and/or curved connection. In some embodiments, the side wall 408 and/or the lower surface 406 defines an opening 410 sized and configured to receive a projection 322 there through. The augment 400a is sized and configured to fill one or more bone voids in a talus during a revision procedure. The talar augment 400a can have any suitable shape for filling a bone void, such as, for example, an oblong shape as shown in FIGS. 18A-18B.

Figure 18C:
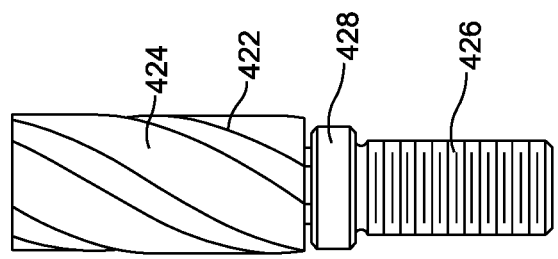

In some embodiments, the bottom surface 406 of the talar augment 400a defines a screw hole 420 sized. In some embodiments, a screw 426 is coupled to a poly driver 422 (see FIG. 18C) and inserted into screw hole 420. The poly driver 422 includes a handle portion 424. A screw head 428 interfaces with a distal portion of the poly driver 422 to allow a surgeon to drive the screw 426 into the screw hole 420. Although a poly driver 422 is illustrated, it will be appreciated that other driver mechanisms can be employed and are within the scope of this disclosure.

Figure 19A:
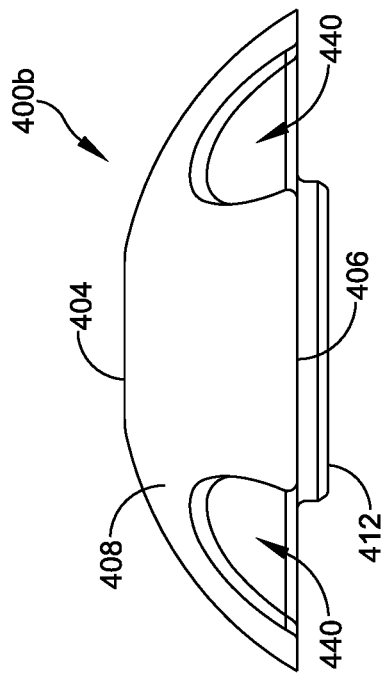
FIGS. 19A-19B illustrate a talar revision augment having a generally circular body, in accordance with some embodiments.
Figure 19B:
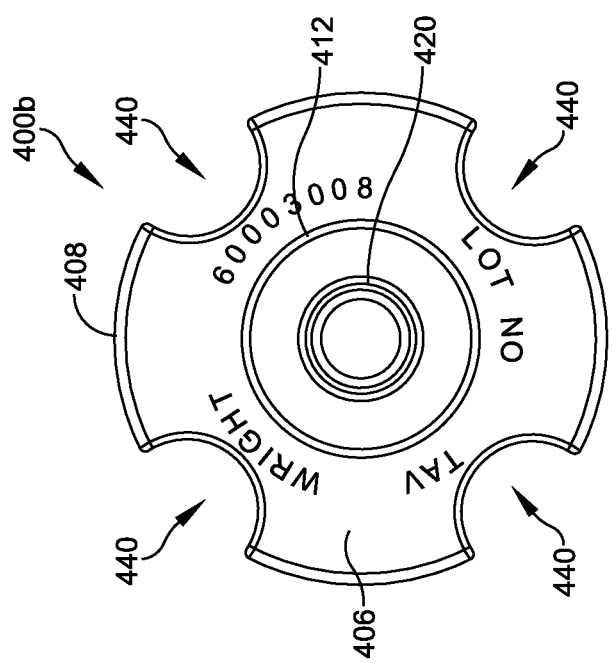
Figure 21A:
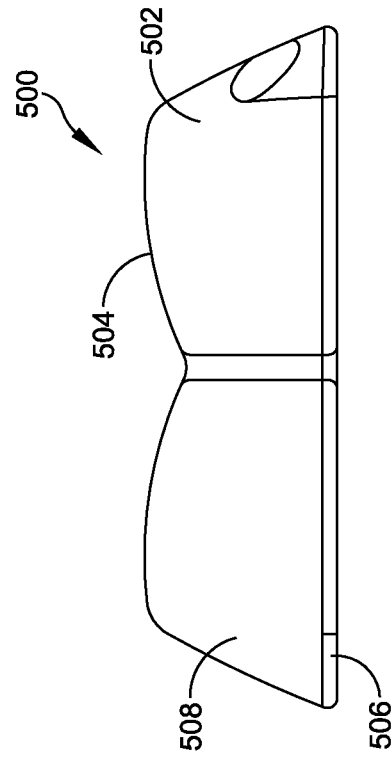
Figure 21B:
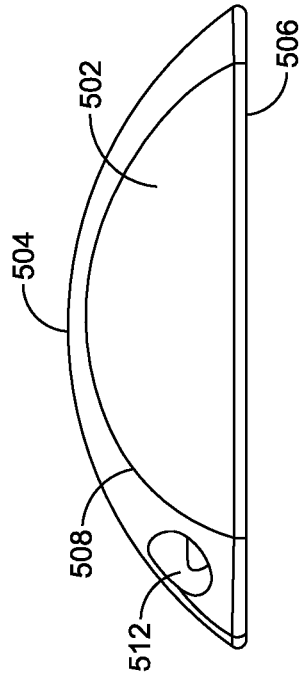

FIGS. 19A-19B illustrate another embodiment a talar augment 400b. The talar augment 400b is similar to the talar augment 400a described in conjunction with FIGS. 18A-18C, and similar description is not repeated herein. The talar augment 400b has a rounded and/or partially circular shaped body 402. One or more cutouts 440 are defined by the body 402 extending from the side wall 408 at least partially into the body 402. In some embodiments, the cutouts 440 are sized and configured to receive a portion of a bone therein. In other embodiments, the cutouts 440 are sized and configured to accommodate one or more pegs 320 when the augment 400b is coupled to a talar plate.

FIG. 20 illustrates one embodiment of a talar plate 300p having a talar augment 400c coupled thereto. The talar plate 300p includes a plurality of pegs 320 extending therefrom (see FIG. 12). The talar augment 400c is sized and configured to couple to the talar plate 300p using the screw 426 and/or any other suitable attachment device. The talar augment 400c fills a bone void in a talus during a revision procedure. In some embodiments, the talar augment 400c is permanently coupled to the talar plate 300p. In some embodiments, the talar augment 400c can be selectively coupled to the talar plate 300p by a surgeon during a revision procedure. The talar augment 400c includes dome-shaped body 402 having a plurality of cutouts 440 formed therein. The plurality of cutouts are sized and configured to receive one or more pegs 330 therethrough. In some embodiments, the talar augment 400c includes a stem hole 420 formed in an upper surface 404, such as, for example, at the apex of the dome-shaped body 402.

In some embodiments, a total ankle revision includes a talar dome primary prosthesis and/or a revision talar dome. FIGS. 21A-21D illustrate one embodiment of a revision talar dome 500 sized and configured to replace a primary talar dome during a revision procedure. The talar dome 500 includes a body 502 extending between an upper surface 504 and a lower surface 506. The upper surface 504 defines an articulating surface having a convex or saddle-shape. The articulating surface is sized and configured to articulate against a tibial platform 132 received in a tibial revision implant component. The lower surface 506 is a planar surface. In some embodiments, a head opening 514 extends from the lower surface 506 at least partially into the body 502. The head opening 541 is sized and configured to receive a head extending from one or more ankle prosthesis components, such as a talar revision plate, therein. The head opening 514 can be centrally located on the lower surface 506 and/or can be offset from the center. In some embodiments, the revision talar dome 500 includes a plurality of clearance holes 510 extending from the lower surface 506 at least partially into the body 502. The plurality of clearance holes 510 are sized and configured to receive at least an upper portion of a fastener therein. For example, in some embodiments, the plurality of clearance holes 510 are configured to receive an upper portion of one or more fasteners inserted into a talar plate.

As described above, the revision implant components/augments can have a variety of shapes and geometries. In some embodiments, the revision implant components/augments are formed from a plasma sprayed titanium, although other materials including, but not limited to, BIOFOAM®, available from Wright Medical Technology, Inc., and other metal, ceramic, plastic, and bone growth materials.

The size and shape of the components of the total ankle revision system 2 can be selected after pre-operative assessment using fluoroscopy to identify the position of a multi-component prosthesis that is implanted in bone, or the selection of the appropriate revision implant component/augment 4-10 can be performed intraoperatively by a surgeon or other healthcare provider after reviewing the implant site. In some embodiments, the revision implant components/augments 4-10 are individually sterilized and packaged while in some embodiments the implant components/augments 4-10 are provided in a kit. For example, when provided in a kit, each individual implant component/augment 4-10 may be individually packaged and included in a larger container or packaging. However, kits can also be formed without packing multiple implant components/augments 4-10 in a single package.

During a revision operation, a multi-component prosthesis 100 that was previously implant in a patient may be partially or completely disassembled. For example, if the multi-component implant 100 includes a tibial platform 102, a tibial tray 4, and a talar dome 6, then the surgeon can decouple the tibial platform 102, the tibial tray 104, the talar dome 106 using a tool such a screw driver, a dowel, or a specialized instrument as will be understood by one of ordinary skill in the art. For example, a tibial platform 102 can be separated from a tibial tray 104 by disengaging the Morse taper or unscrewing the implant components. If, for example, the multi-component prosthesis 100 is a talar prosthesis, then the talar dome 6 can be decoupled from talar stem (not shown) by disengaging the Morse taper coupling. When completely disassembled, the entire multi-component prosthesis is removed from the patient.

With the multi-component implant at least partially disassembled, one or more revision implant components/augments 4-10 are assembled to the multi-component prosthesis in situ using the applicable attachment mechanism. In some embodiments, the in situ attachment includes inserting one or more revision implant components/augments 4-10 into a pre-existing intramedullary cavity and attaching the revision implant components/augments 4-10 to the implanted component(s) of the multi-component prosthesis. It is also possible to couple together one or more revision implant components/augments 4-10 with one or more components of the multi-component prosthesis ex situ and then couple the resulting assemblage to any components of the multi-component prosthesis. For example, if the multi-component implant is completely removed from the patient, the surgeon or another medical professional or care giver can implant one or more components of a multi-component prosthesis with one or more revision implant components/augments 4-10.

As described above, the components of the total ankle revision system 2 can have different shapes from each other and/or from the shapes of the other components of the total ankle revision system 2. The components of the total ankle revision system 2 are coupled together to fill a void in a bone. Additionally, a single component/augment can include multiple attachment means, such as, for example, a taper, threads, a bayonet coupling, to list but only a few possibilities.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A revision implant, comprising:
   a body extending between a first planar surface and a second planar surface;
   a head extending from the first planar surface of the body and configured to couple the revision implant to an additional component of a multi-component prosthesis;
   at least one coupling mechanism configured to couple the body to a first bone, wherein the at least one coupling mechanism comprises one or more protrusions extending from the second planar surface of the body; and
   a dome-shaped projection extending from the second planar surface and defining a first fastener hole configured to receive a fastener coupling an augment to the body, where the augment is configured to fill a void of the first bone;
   wherein the head defines a second fastener hole configured to receive the fastener.

2. The revision implant of claim 1, comprising said fastener configured to extend through said first and second fastener holes and couple the body of the revision implant to the augment.

3. The revision implant of claim 1, wherein the head defines a cylindrical-shaped protrusion.

4. The revision implant of claim 3, wherein the head defines an alignment groove extending from a first side to a second side of the cylindrical-shaped protrusion.

5. The revision implant of claim 1, wherein the one or more protrusions extend from the second planar surface of the body at a predetermined angle.

6. The revision implant of claim 5, wherein the predetermined angle comprises an angle between 5-90°.

* * * * *